Figure 1A:
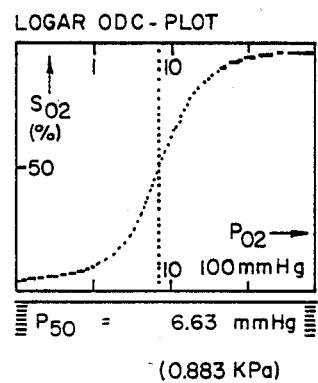

United States Patent [19]

Feller et al.

[11] Patent Number: 4,920,194

[45] Date of Patent: Apr. 24, 1990

[54] BLOOD SUBSTITUTE

[76] Inventors: Wolfgang Feller, Ernstbergstrasse 30; Norbert Macht, Hessenwinkel 26, both of Melsungen; Johannes G. Böttrich, Talstrassse 6, Kirtorf-Lehrbach, all of Fed. Rep. of Germany

[21] Appl. No.: 110,013

[22] Filed: Oct. 19, 1987

[30] Foreign Application Priority Data

Oct. 28, 1986 [DE] Fed. Rep. of Germany ....... 3636590

[51] Int. Cl.$^5$ ...................... C07K 15/22; A61K 37/14
[52] U.S. Cl. ......................................... 530/385; 514/6; 424/101
[58] Field of Search ........................... 314/6; 530/385; 424/101

[56] References Cited

U.S. PATENT DOCUMENTS

| | | | |
|---|---|---|---|
| 4,001,200 | 1/1977 | Bonsen et al. | 530/385 |
| 4,001,401 | 1/1977 | Bonsen et al. | 514/6 |
| 4,061,736 | 12/1977 | Morris et al. | 514/6 |
| 4,401,652 | 8/1983 | Simmonds et al. | 514/2 |
| 4,547,490 | 10/1985 | Ecanow et al. | 514/2 |

OTHER PUBLICATIONS

Chem. Abs., 85:15747c, "The Effect of Heparin on the Function and Structure of Adult Human Hemoglobin", Rucheaul, K. et al. (1975).

*Primary Examiner*—Howard E. Schain
*Assistant Examiner*—Susan M. Perkins

[57] ABSTRACT

The invention relates to stroma-free blood substitutes, which are characterized in that fragments, prepared in a per se known manner, of sulfated glycosaminoglycans are covalently linked with hemoglobin to form products the oxygen binding property of which may be adjusted to be within the range of from 2.66 kPa (20 mmHg) to 10.66 kPa (80 mmHg), and preferably to within the range of from 4.79 kPa (36 mmHg) to 9.33 kPa (70 mmHg) by pre-determining the ratio of hemoglobin to glycosaminoglycan fragment, and to a process for preparing blood substitutes.

18 Claims, 21 Drawing Sheets

P(50) = 6.42 mmHg (0,854 KPa)
N(40-60%) = 2.25

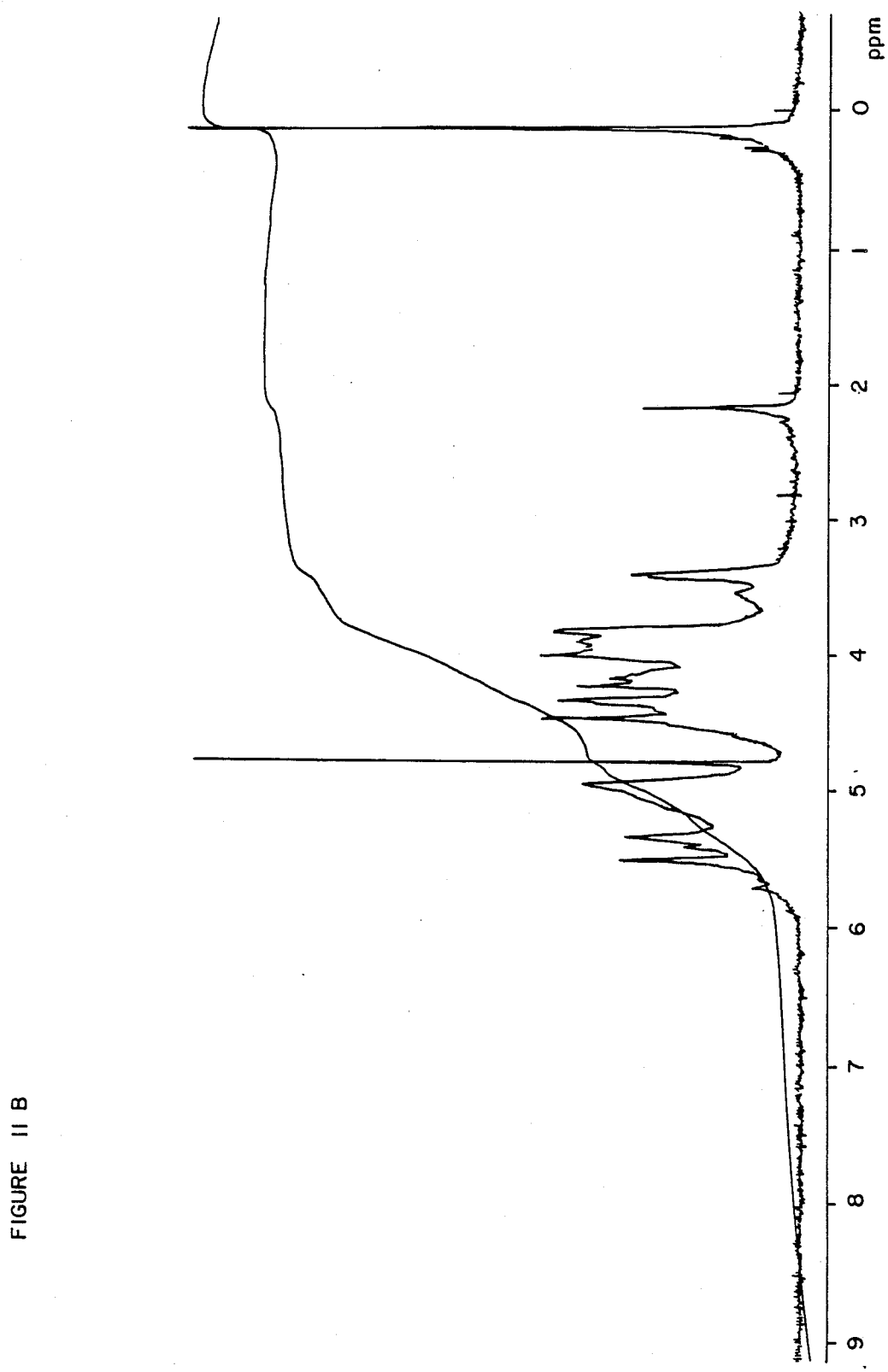
FIGURE II B

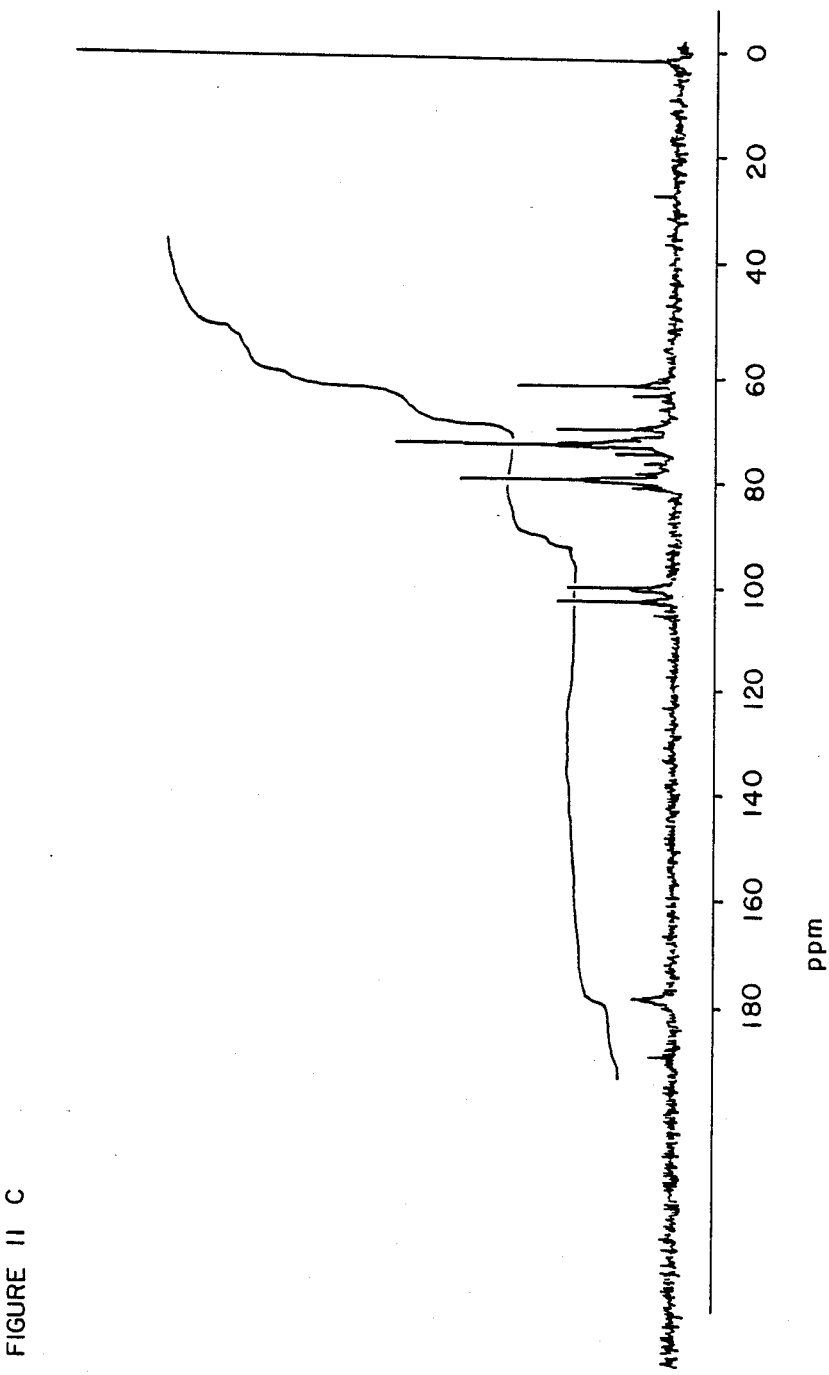
FIGURE II C

BLOOD SUBSTITUTE

The present invention relates to new blood substitutes containing hemoglobin and to processes for preparing same and the use thereof as medicaments.

Aqueous solutions containing human or animal hemoglobin and reversibly absorbing or releasing oxygen have been worldwide investigated for many years in order to find out whether they are capable as a volume substitute with oxygen-transferring function to reduce or compensate for ischemia caused by massive blood loss.

Upon a first view, aqueous hemoglobin solutions might be suitable as ideal plasma expanders having colloid-osmotic oxygen- and carbon dioxide-transporting properties. Moreover, it may be expected that pure hemoglobin solutions do not exhibit any blood group properties so that per se best conditions should exist for a general application to humans.

Rabiner et al. showed in animal-experimental investigations already in 1967 (J. Exper. Med. 126, 1127) that stroma-free hemoglobin solutions can be infused without adversely affecting the kidney function and without affecting the clotting system. Pre-requisite for this good compatibility was the separation of the "stroma" containing lipids, i.e. the cell membrane fragments of the erythrocyte membrane which caused the nephrotoxicity observed previously.

However, later on it has been shown that substantially two crucial properties of the stroma-free human hemoglobin solutions bar the medical use thereof.

The intravasal half-life time, i.e. the time during which the hemoglobin concentration upon intravenous administration decreases to 50% of its initial value is very short and, depending on the dosage, ranges at from only two to four hours.

The cause thereof is provided by the molecular structure of human hemoglobin. Native hemoglobin having a molecular weight of 64,500 consists of four sub-units having the tetramer structure $\alpha_2\beta_2$, which under physiological conditions in its oxygenated form (R=Relaxed-state) is in equilibrium with about 4% of a dimer $\alpha\beta$ having the molecular weight of about 32,000. These hemoglobin dimers, due to the low molecular weight thereof, may be secreted through the kidneys.

The pressure of half-saturation (P50 value) of a conventional solution of pure stroma-free hemoglobin (which is to be considered as a measure of the oxygen-binding property) is from about 0.40 kPa (3 mmHg) to 0.93 kPa (7 mmHg) of oxygen partial pressure. In comparison thereto, the oxygen partial pressure at half-saturation of hemoglobin in intact erythrocytes under physiological conditions is from 3.33 kPa (25 mmHg) to 3.72 kPa (28 mm Hg). The increased oxygen affinity of the conventional stroma-free Hb solution has as result that, although oxygen can be absorbed in the lungs from the hemoglobin, said oxygen can be released again only at a reduced rate in the peripheral tissue at $O_2$ partial pressures around 5.3 kPa (40 mmHg).

FIG. 1 shows oxygen binding curves of human erythrocytes and of a stroma-free Hb solution. The "leftward shift" of the hemoglobin solution towards lower $O_2$ partial pressures is clearly visible. Measurement conditions: Buffer: 225 mM of BISTRIS, pH 7.4; temperature of measurement: 37° C., Hb-concentration = 60 mg/ml.

In order to overcome these two problems, namely to achieve a decrease in the oxygen affinity and an increase in the intravasal half-life time or residence time, respectively, in the past several experimental approaches have been started for preparing a stroma-free hemoglobin which does not have said disadvantageous properties. The goal always was to develop a preparation meeting the following requirements:

1. The intravasal half-life time (as a measure for the intravasal residence time) for hemoglobin solutions should be 10 to 30 hours.
2. The stroma-free hemoglobin solution reversible transfers oxygen and carbon dioxide. The half-saturation pressure (P 50 value) of the oxygen binding curve of a hemoglobin solution under physiological conditions should at least be from 3.33 kPa (25 mmHg) to 3.72 kPa (28 mmHg).
3. The solution should be oncotic and have colloid-osmotic pressures of from 3.33 kPa (25 mmHg) to 4.00 kPa (30 mmHg).
4. The solution should be storage-stable. It is desired that the preparation may be stored for about one year—if possible without being cooled or even frozen.
5. The solution should have flow properties comparable to the blood viscosity. Lower viscosities than that of blood are acceptable.
6. The ionic composition should be such as to ensure an osmolarity of from 260 to 320 mOsm and be comparable to the ionic composition of human blood.
7. The solution is sterile, pyrogen-free and free from virus particles (e.g. hepatitis, AIDS).
8. The solution does not have any blood group properties.
9. The methemoglobin content is below 5%, based on the total hemoglobin concentration.
10. The solution does not contain any stroma components.
11. The oxygen binding and release properties allows the patient to breathe-in air for sufficient oxygen supply to the peripheral tissue. An additional enrichment with $O_2$ is not necessary. The amount of oxygen bound to human hemoglobin in an erythrocyte is around 1.34 ml of oxygen per 1 g of hemoglobin. Under regular conditions this value should also be attained by the hemoglobin solution.
12. The solution contains as little auxiliary materials as possible in concentrations as low as possible.
13. The solution is inexpensive, reproducible and producible with high yields—based on hemoglobin.
14. The solution must be compatible also in high doses and must not cause any immunological reactions to occur.
15. The toxicity of the solution is low. More specifically, the catabolism of the intravasally administered hemoglobin must not adversely affect the reticuloendothelial system and/or the kidney functions. All organ functions will be maintained during and after the application of the hemoglobin solution. Chronic deteriorations of the organ function will not occur after application of the Hb solution.

In order to achieve a better understanding of the described methods for preparing a stroma-free hemoglobin solution, it will be necessary to explain the hemoglobin structure in greater detail:

The human hemoglobin tetramer having a molecular weight of 64,500 is composed of four nearly identical moieties. The hemoglobin tetramer $\alpha_2\beta_2$ of hemoglobin A (HbA), the most important and, with the respect to its proportion in blood, normally most abundant hemoglobin, consists of two pairwise identical $\alpha$- and $\beta$-chains.

The molecular weight of the α-chain is 16,400, and that of the β-chain is 15,850.

Hemoglobin A altogether contains 42 lysine moieties which are accessible to a chemical modifying reaction using reactive cross-linking agents specific to amino groups such as, for example, glutardialdehyde.

The tetramer may exist in two different conformations, the R (Relaxed) or the T (Tense) form, which, however, are distinguished by their oxygen affinity, the T form having a higher affinity to oxygen. The affinity to oxygen of the human hemoglobin in the erythrocyte is controlled by 2,3-diphosphoglycerate (2,3-DPG). An increase in the DPG content in erythrocytes leads to a decrease in the oxygen affinity and, thus, causes a "rightward shift" of the oxygen binding curve. 2,3-DPG binds at a position known as phosphate binding site or "β-cleft" of the hemoglobin molecule and, thus, caused ionic "bonds" to be formed, whereby the two phosphate groups with 4 histidine moieties of the hemoglobin and the terminal amino groups of the β-chain and the carboxyl group of the 2,3-DPG with the lysine moiety 82 of the β-chain effect a stabilization of the "low affinity" form of the hemoglobin. Other anionic oder polyanionic substances such as, for example, inositol phosphates, and more specifically inositol hexaphosphate, inositol hexasulfate or pyridoxal phosphate, basically act in the same manner as 2,3-DPG with human hemoglobin and decrease the oxygen affinity in part to a higher degree than 2,3-DPG does.

The routes described in the literature for solving the problem of preparing a hemoglobin solution may be grossly classified by the principles of the used methods:

(a) Intermolecular or intramolecular cross-linking of hemoglobin using bi- or polyfunctional cross-linking agents.

(b) Cross-linking of hemoglobin using bi- or polyfunctional reactive cross-linking agents with an additional modifying step, for example using pyridoxal phosphate, with the goal of at least compensating for the increase in the oxygen affinity due to cross-linking or even achieving an improvement.

(c) Covalent linking of hemoglobin to water-soluble, physiologically compatible polymers such as dextran, polyvinyl pyrrolidone, hydroxyethyl starch, inulin, or to polyethylene glycol or polypropylene glycol as well.

(d) Non-covalent (ionic) linking of hemoglobin to water-soluble, physiologically compatible polymers containing anionic groups as ligands, such as inositol hexaphosphate. These polymer-bonded groups have a high binding affinity to hemoglobin.

(e) Reaction with modifying reagents which leads to either an intermolecular or an intramolecular cross-linking of the hemoglobin tetramers and at the same time cause a "rightward shift" of the oxygen binding curve. These modifying reagents contain reactive functional groups in the molecule capable of covalently reacting with functional (amino) groups of the hemoglobin as well as anionic molecule portions reducing the oxygen affinity upon binding to the phosphate binding site of the hemoglobin. 2-Nor-2-formyl-pyridoxal-5-phosphate may be mentioned as an example.

(f) Inclusion of hemoglobin in liposomes, so called hemosomes.

(g) Combination of invidual routes for solving the problem.

In the DE-OS 24 17 619, for example, there have been described plasmaprotein substitutes containing hemoglobin and the subunits of which are reacted with dialkyl dicarboxylic acid imidates to form polymeric products having average molecular masses of from 68,000 to 600,000.

In the DE-OS 26 07 706 there have also been disclosed water-soluble hemoglobin products the subunits of which are cross-linked by using suitable cross-linking agents such as, e.g., triazines, polysubstituted polyfunctional benzene derivatives, linear or cyclic polyfunctional poly-alkylene derivatives, dicarboxylic acid derivatives or dialdehydes to form polymers having molecular masses of from 64,000 to 1,000,000 D.

In order to increase the intravasal residence time of a stroma-free hemoglobin solution attempts have also been made to covalently bind hemoglobin to physiologically acceptable highly polymeric substances. As the physiologically compatible polymers there were described, in particular, hydroxyethyl starch (DE-OS 26 16 086) and further polysaccharides covalently bonded through bridges (DE-OS 30 29 307), inulin (EP-A 81 302 858.6), dextran [S. Thamon, J. Blumenstein and J. T. Wong, P.N.A.S. 73, 2128 (1976); R. G. Humphries et al., P.B.S., 191 (1981); J. E. Baldwin et al., Tetrahedron 37, 1723 (1981)]or polyethylene glycols of various molecular masses [K. Ajisaka et al., B.B. Res. Comm., 97, 1076 (1980); U.S. Pat. No. 4,301,144].

Nevertheless, any modification whatever of the hemoglobin molecule will always imply a simultaneous alteration in its natural quaternary structure and—due thereto—will influence the oxygen binding property by significantly reducing the Hill coefficient and the P 50 value.

Deoxygenated modified hemoglobin, although it is capable of binding oxygen, cannot release said oxygen to the peripheral tissue in an amount required because of the increased affinity of the system $Hb/O_2$.

Figure 1B:
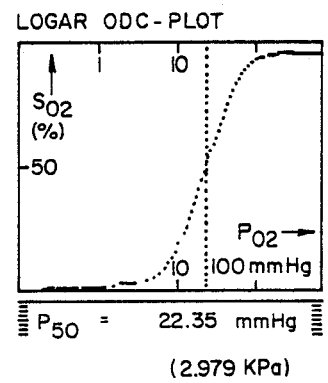

This phenomenon may be quantitatively measured by recording an oxygen binding curve (oxygen dissociation curve); the binding curve of the modified hemoglobin (cf. FIG. 1A) is shifted to the left, i.e. towards lower oxygen partial pressures, as compared to that of chemically unchanged hemoglobin (cf. FIG. 1B).

All of the cross-linking reactions and methods of covalent coupling to water-soluble polymers as so far known have in common that the P 50 value decreases against that of un-polymerized hemoglobin. Furthermore, a decrease in hemoglobin cooperativity has been observed. Thus, the Hill coefficient, rated as a measure for this cooperativity, decrease from 2.8 to values below 2.

In 1969 Benesch et al. for the first time described the influence of pyridoxal phosphate on the decrease of the oxygen affinity of hemoglobin. After it had been successfully achieved to chemically couple pyridoxal phosphate to HbA, pyridoxalated hemoglobines were used in various laboratories for obtaining polymerized and at the same time pyridoxalated hemoglobin products having oxygen half-saturation pressures of about 3.6 kPa (27 mm Hg) (German Patent 31 44 705 C2).

It is applicable to all hemoglobin cross-linking reactions—such as, for example, with glutardialdehyde—that the cross-linking process is very difficult to control and reproducible cross-linking products are obtained only in a gross approximation, while losses in yield have also to be tolerated. Furthermore, the colloid-osmotic activity of these polymers often is so low that for correcting the COP further expensive additives such as albumin must be added (German Patent 31 44 705 C2).

Moreover, as the viscosity of the cross-linked product has been much increased, with simultaneous decrease in water solubility, in comparison to hemoglobin solutions having the same concentrations, it was attempted in the following time to employ defined "modifying agents" which effect intramolecular cross-linking in the tetramer structure and at the same time reduce the oxygen-binding affinity.

In 1975 Benesch et al. described the reaction of oxygenated hemoglobin with 2-Nor-2-formylpyridoxal-5-phosphate. It could indeed be determined that the product obtained by intramolecular cross-linking is only very slowly secreted in the animal test. Said product had an intravasal half-life time of $T_{\frac{1}{2}}=24$ hours at an oxygen half-saturation pressure of P 50=3.46 kPa (26 mmHg) to 3.72 kPa (28 mmHg). What is disadvantageous is the very laborious synthesis of this modifying agent. In the U.S. Pat. No. 4,529,071 there has been described the intramolecular cross-linking in stroma free tetrameric deoxy-hemoglobin using diaspirin esters and subsequent modification with pyridoxal phosphate. The obtained products exhibit half-saturation pressures of 3.33 kPa (25 mmHg) to 4.65 kPa (35 mmHg). In the animal experiment using rabbit an intravasal half-life time of about 20 hours was recorded at a dosage of 200 mg/kg.

However, there is an inherent drawback in that several reactions of hemoglobin are required, namely those with the diaspirin esters, pyridoxal phosphate and NaBH$_4$.

In the U.S. Pat. No. 4,473,496 there are described phosphorylated ribose derivatives oxidized with periodate which start from adenosine-5'-triphosphate or from 5-phosphoribosyl-1-pyrophosphate which with hemoglobin form intramolecularly cross-linked products. The obtained P 50 values are about 4.65 kPa (35 mmHg).

Therefore, it is the object of the present invention to provide new hemoglobin products by way of one simple reaction using only a single modifying agent, the P 50 value of which hemoglobin products is freely adjustable within wide limits, depending on the requirements, between 2.66 kPa (20 mmHg) and 10.64 kPa (80 mmHg), and preferably between 4.79 kPa (36 mmHg) and 9.33 kPa (70 mmHg).

The need of adjusting the stroma-free Hb solutions to a higher O$_2$ half-saturation pressure (P 50 value) than 3.59 kPa (27 mmHg) will be apparent from the following considerations:

The results of model calculations (Dissertation W. Gauch, Aachen, West-Germany, 1986) show that the arteriovenous difference of oxygen saturation and oxygen concentration as a measure for the "exhaustion" of the oxygenated hemoglobin in blood in relation to the P 50 value passes a maximum under otherwise equal breathing conditions.

The result of these calculations is that the exhaustion of the oxygen bonded to hemoglobin passes a maximum within the range of the P 50 value of from 5.32 kPa (40 mmHg) to 7.98 kPa (60 mmHg). Therefore, it is not sufficient to adjust the P 50 value of a blood substitute containing hemoglobin to about 3.33 kPa (25 mmHg) to 3.72 kPa (28 mmHg), but the oxygen exhaustion may be further maximized if the P 50 value is shifted into the range as mentioned. For example, a model calculation shows that it is possible to achieve an increase of the arterio-venous saturation difference by 2.5 times, if the P 50 value in an erythrocyte is changed from 3.59 kPa (27 mmHg) to 8.25 kPa (62 mmHg). It is independent thereof whether in vivo further mechanisms of compensation (e.g. alteration of the heart time volume) come into effect which mechanisms may be able to make up for the reduced hemoglobin content such as upon loss of blood.

It is, therefore, another object of the present invention to develop a process for being able to shift the P 50 value of hemoglobin solutions to within the range of the P 50 calculated to be the "optimum" at which a maximum oxygen exhaustion of the hemoglobin is to be expected. Hemoglobin solutions having optimum P 50 values allow the following advantages to be expected over the existing approaches to solve the problems:

In comparison to solutions having not the optimum P 50 value, smaller volumes of solutions having the optimum P 50 value may be administered, as the oxygen exhaustion of the preparation has been optimized.

Therefrom it ensues that a substantially higher efficiency, based on the employed hemoglobin, can be attained.

It has been known that the oxygen affinity and, hence, the P 50 value, of hemoglobin A may be influenced by polymeric polyanions such as heparin or dextrane sulfate [P. Labrude et al. Hemoglobin Solutions as Oxygen Carriers: Ligands and Other Molecules Interactions with Hemoglobin in: Adv. Biosci. 1986, 54 (Oxygen Transp. Red Blood Cells), page 16 et seq., and Amiconi, G. et al. Eur. J. Biochem. 76, 339–343 (1977)].

Dependent on the concentration, the P 50 value of the hemoglobin increases at increasing heparin concentration to values of from 7.98 kPa (60 mmHg) to 10.64 kPa (80 mmHg). In a publication "Interaction Between Human Hemoglobin And Sulfated Polysaccharides: Identification Of the Binding Site and Specificity" in: Affinity Chromatography and Biological Recognition, Ed. I. M. Chaiken, M. Wilchek, I. Parikh, Academic Press, 1983, it has been stated that in mixtures comprising HbF, HbA, HbS and HbC under the conditions of a gel electrophoresis in agar gel an unusual separation behavior of hemoglobin occurs. This effect failed to occur if agar was replaced by agarose or agarose gel having a low sulfate content.

In said publication it has further been determined that the gelation behavior of sickle cell hemoglobin (HbS) is inhibited by fucoidan, γ-carragenan, dermatan sulfate and heparin, however not by hyaluronic acid or chondroitin-4- or -6-sulfate. Furthermore, by column chromatography an interaction of purified hemoglobin with γ-carragenan is detected, and the association constants with HbF, HbA and HbS are determined.

Therefore, it may be considered as having been known that polyanionic polymers such as, e.g., heparin, dextran sulfate or dermatan sulfate form associates with hemoglobin in aqueous solution which associates, depending on the concentration, increase the P 50 value thereby decreasing the oxygen affinity of human hemoglobin(s).

However, some experiments using heparin show that, although the bonding of heparin to hemoglobin A is relatively strong, nevertheless relatively high heparin concentrations have to be chosen in order to achieve a shift of the P 50 value into the range of about 6.65 kPa (50 mmHg).

Thus, the P 50 value of a stroma-free hemoglobin solution containing 67 mg/ml of HbA is shifted from 0.66 kPa (5 mmHg) to 8.25 kPa (62 mmHg), after 10 mg/ml of heparin have been added. The conditions of measurement for determining the oxygen binding curve are: 225 mM of BISTRIS buffer, pH 7.4, 37° C.

Commercially available heparin consists of a mixture comprising sulfated glycosaminoglycan chains falling in the molecular weight range of from about 3,000 to 30,000. The maximum of the molecular weight distribution is at a molecular weight of about 12,000 to 15,000.

Commercially available heparin is a natural product and is mainly recovered from the lungs and intestine mucous membrane (mucosa) of slaughter cattle. Most widely spread in the trade are heparin salts in the sodium and calcium forms isolated from the mucosa of horned cattle and hogs and from the lungs of horned cattle. In medicine, heparin is employed as an antithrombotic agent in the prophylaxis of thromboses and thrombo-embolisms as well as in therapeutic doses for the treatment of thromboembolic complications and in extracorporeal blood circulating systems.

The most significant side-effect of heparin consists of that, more specifically at higher doses, bleeding complications may occur due a blockade of the plasmatic clotting system and an influence on the thrombocytes.

The biological activity of heparin may be determined by means of clotting tests such as the test according to U.S.P. XX using sheep plasma or the apTT (activated thromboplastin time). The activity is expressed in International Units. As the standard for the above-mentioned tests there is used a Comparative Heparin established by the WHO, at present the 4th WHO Heparin Standard.

Furthermore, chromogenic substrate tests are frequently used which utilize the heparin-catalysed inhibition of thrombin or factor Xa as the test principle.

The anti-coagulative heparin activity—measured by means of the apTT or the test according to U.S.P. XX—decreases with decreasing molecular weight of the heparin. The activity of commercially available heparin is about 150 I.U./mg.

The chemical structure of heparin mostly consists of recurring sequences of the triply-sulfated disaccharide $I_{2S}$-$A_{NS,6S}$ ($\alpha$-1,4-L-iduronic acid-2-sulfate)-(D-glucosamine-N,6-disulfate). This structure element normally occurring in heparin may be interrupted or replaced by several sequences. B. Casu presents a survey on the average heparin structure in Nouv. Rev. Fr. Haematol., 26, 211-219 (1984).

Heparins may further be electrophoretically separated into two fractions in basic buffers in the presence of polyvalent cations, the so-called fast-moving component and the so-called slow-moving component.

Furthermore, there exist differences in the structures, depending on from which organ the heparin has been recovered. By means of NMR spectrometry ($^1$H and $^{13}$C) type A (mucosa) and typ B (lungs) heparins are distinguishable.

In summary it may be stated that heparin is a heterogeneous substance mixture which may be distinguished from other glycosaminoglycanes, for example, by the features of
origin (animal species)
kind of the salt (e.g. sodium or calcium)
molecular weight and/or molecular weight distribution
ratio of fast/slow-moving components
anionic density
degree of sulfation
contents of N-acetyl or N-sulfate groups
types A or B
biological activity, e.g. anticoagulative activity
affinity to plasma proteins such as, for example, immobilized AT III.

As has already been mentioned, the influence of heparin on the P 50 value of the hemoglobins is increased, if heparins having a lower molecular weight than that of commercially available heparin are mixed with hemoglobin in different concentrations are mixed under defined conditions (pH, temperature, ion strength, buffer).

In the literature there have been described numerous methods for chemically or enzymatically cleaving commercially available heparin into fragments or to prepare or isolate, respectively same by means of per se known methods such as gel filtration, steps of fractionating precipitations using organic solvents or ultrafiltration.

A survey on the common methods is presented in the article as already quoted by Casu. Reference may further be made to the publication by B. Casu "Structure and Biological Activity of heparin" in "Advanced Carbohydrate Chemistry and Biochemistry". Thus, the methods cited for the separation and cleavage of heparin and other sulfated glycosaminoglycanes have basically been known.

The cleavage reactions of heparin as known from the literature include some reactions, more specifically the cleavage with $HNO_2$ and $NaIO_4$, which lead to heparin and/or heparin fragments having reactive aldehyde groups.

1. Nitrous acid cleaves the glycosidic bond between the glucosamine-N-sulfate residue and the uronic acid residue of heparin, so that reactive 2,5-D-anhydromannose residues are formed at the reducing end of the heparin degradation product. Nitrous acid reacts with the free amino groups of the glucosamine moieties of heparin, which to a low portion are already present in the commercially available heparin (10 to 50 $\mu$mol/g) or are formed under the reaction conditions in the acidic pH range by N-deacetylation or N-desulfation.

Nitrous acid may be generated in situ by very different processes as known to the artisan. The simplest route is to add nitrite (e.g. sodium nitrite) to aqueous heparin solutions in an acidic pH range and to allow the reaction to proceed at a pre-determined temperature in the range of from 2 to 60° C. As an example for another preparation variant there may be mentioned the depolymerization of heparin with $HNO_2$ in 1,2-dimethoxyethane at −20° C. The extent of cleavage is determined by the reaction conditions, and more particularly by the ratio of heparin to nitrite. In order to obtain fragments as small as possible, a high excess of nitrite is employed. The pH value affects the course of the reaction to the effect that, although the degradation (cleavage) reaction proceeds faster, in the more acidic range an increasing occurrence of competitive reactions such as N-desulfation, O-desulfation as well as hydrolysis of the N-acetyl groups in the initial heparin and in the reaction products is to be expected. Systematic investigations showed that a pH range of from 2 to 6, and preferably around 4.0 may be employed for the reaction.

2. Furthermore, heparin may be subjected to periodate oxidation at the $C_2$-$C_3$ bond of unsulfated uronic acid moieties, and then the dialdehydes thus produced may be treated with alkali hydroxide solutions. This degradation also provides fragmentation products having low molecular weights and at the same time bearing reactive aldehyde groups. A description of a procedure for oxidizing heparin with periodate is given in: B. Casu et al., Arzneim. Forschung/Drug Res. 36(I), Nr. 4 (1986), pp. 637 et seq.

3. Furthermore, low molecular weight heparin fractions may first be prepared from commercially available heparin by means of known process such as the enzymatic degradation using a heparinase or a hydrazinolysis or a fractionating process using ultrafiltration, a fractionated precipitation with organic solvents or gel filtrations, and these cleavage products or fractions may be subjected to a further degradation using $HNO_2$ and/or to a periodate oxidation with $NaIO_4$.

4. Another possibility of obtaining defined heparin fragments comprising reactive aldehyde groups consists of first subjecting heparin to a cleavage with $HNO_2$ according to 1. and then reacting the product with sodium periodate in a consecutive step according to 2. The sequence of the two steps may be reversed.

5. Furthermore, heparin or any heparin cleavage products prepared otherwise may be activated with activating reagents such as cyanogen bromide or EDC {1-ethyl-3-(3-dimethylaminopropyl)-carbodiimid}.

Such activating reagents for polysaccharides and proteins are known to an artisan from the affinity chromatography or chemistry for protein immobilization (cf. "Methods in Enzymology" Volumes 44 and 34 and "Introduction to Affinity Chromatography", C. R. Low, North-Holland, 1979, Ed.: T. S. Work, E. Work).

Thus, for example, the carboxyl group of heparin may also be activated with N-hydroxysuccinimide by means of dicyclocarbodiimides.

The U.S. Pat. No. 4,496,550 describes the preparation and use of oligosaccharides (heparin fragments) prepared by heparin-cleaving methods:

(a) Heparin is treated with $HNO_2$ in 1,2-dimethoxyethane.

(b) Heparin is reacted with nitrite in aqueous solution.

(c) Heparin is treated with periodate at a low pH value and at a low temperature.

(d) Heparin is enzymatically treated with heparinases.

(e) Heparin is depolymerized by first esterifying the carboxyl groups and subsequently subjecting to an alkaline β-elimination.

(f) Heparin is partially depolymerized by a partial N-desulfation which is followed by a step of cleaving with $HNO_2$.

Further methods for effecting a chemical cleavage by use of $H_2O_2$/ascorbate or peracids (radical depolymerization) have also become known (U.K. Pat. Appl. 33615/77; U.S. Pat. No. 4,281,108; EP-Application 012 067).

In "Carbohydrate Research" 138, 199–206 (1985) there has further been set forth a recipe for the exhaustive degradation of heparin from bovine lungs using nitrous acid.

Accordingly, it is the object of the present invention to chemically couple known heparin fragments with hemoglobin present in the form of an aqueous stroma-free solution and thereby to prepare new oxygen-transferring "blood substitutes".

The subject matter of the present invention is a stroma-free blood substitute which is characterized in that fragments, prepared in a per se known manner, of anionic (sulfated) glycosaminoglycans are reacted with hemoglobin which may be of various origin, e.g. human, bovine, porcine, to form covalently linked adducts in such a manner that by pre-determining the ratio of hemoglobin to glycosaminoglycan fragment the oxygen binding property thereof may be adjusted to be within the range of from 2.66 kPa (20 mmHg) to 10.66 kPa (80 mmHg), and preferably to within the range of from 4.79 kPa (36 mmHg) to 9.33 kPa (70 mmHg).

According to the invention it was now found that heparin fragments having molecular weights of from 1,000 to 10,000, and preferably those in the molecular weight range of from 1,000 to 3,000, which simultaneously bear reactive groups such as, for example, may be reacted with hemoglobin to form stable products. In this reaction there are formed stable hemoglobin-heparin fragment adducts the oxygen binding behavior of which, expressed by the P 50 value, can be adjusted to be within the range of from 2.66 kPa (20 mmHg) to 10.66 kPa (80 mmHg).

Other sulfated glycosaminoglycans such as dermatan sulfate of heparan sulfate of course may also be cleft into fragments having reactive terminal groups, and these fragments may be reacted with hemoglobin. It is further possible first to subject the raw materials employed for cleaving to a sulfating step to increase the number of O-sulfate groups. Methods for introducing sulfate groups as N- and O-sulfate esters are known to the artisan. Process variants described by C. R. Ricketts, "Biochem. Journal" 51, 129–133 (1952) or O. Larm et al., "Carbohydrate Research" 73, 332–336 (1979) may be applied.

In this case of an additional introduction of sulfate groups the influence of the heparin degradation products on the P 50 value of the hemoglobin is enhanced, i.e. lower amounts of the fragment do already cause a higher shift of the P 50 value as compared to fragments which were not aftersulfated. It was further found that so-called heparinoids, i.e. substances chemically related to heparin such as Pentosanpolysulfat SP 54 ® of the Company Bene-Chemie, Munich, West-Germany, or Arteparon ®, of the Company Luitpold, Munich, West-Germany, as well as heparin may be activated by reaction with $HNO_2$ and/or sodium periodate and reacted with hemoglobin.

Furthermore, heparin-like sulfated glycosaminoglycans which may be prepared from chitin or chitosan, respectively, and show a biological activity similar to that of heparin are also usable within the scope of the invention, in the same manner as heparin, as starting materials for further degradation reactions. For example, Hirano, S. and Tanaka, T. in "Carbohydr. Res." 137, 205–215 (1985) "Effect of sulfated derivatives of chitosan on some blood coagulant factors" describe chitosan derivatives having heparin activity. These products may also be subjected to further degradation or to an activation by $HNO_2$ The obtained degradation products in turn are reacted with hemoglobin to form adducts the P 50 value of which is shifted towards higher partial pressures.

In the course of the preparation of the heparin fragments the auxiliary materials required for cleaving, and more specifically nitrite, must be removed to a sub-ppm level (<0.1 ppm) in order to avoid undesired reactions (oxidation to form methemoglobin). For the characterization of the heparin fragments bearing reactive (terminal) groups the following data may be used:
Content of free aldehyde groups
Molecular mass
Sodium content
Optical rotation
Sulfur content
Osmolarity
Spectral behavior
Content of residual reagents, particularly nitrite Clotting tests, e.g. according to U.S.P. XX More particularly, in the heparin degradation with $HNO_2$ (sodium nitrite in the acidic pH range), which is very simple to perform, the molar ratio of heparin/-$HNO_2$ may be varied in the range of from 1:0.2 to 1:100. Hereto also cf. Knipmeyer, A. J. K., "Master Thesis", Twente University of Technology (1985).

Due to the additional options of selecting the pH value, temperature and reaction time it is possible to prepare heparin fragments having desired molecular weights and reproducible aldehyde (anhydromannose) contents.

Upon a closer investigation of the hemoglobin-heparin fragment adducts according to the invention it was surprisingly found that the intravasal half-life time hemoglobin-heparin fragment adducts has been much prolonged as compared to chemically unreacted hemoglobin, the prolongation depending on the chosen ratio of heparin/Hb;

the P 50 value is adjustable to a high degree by the ratio of Hb/heparin fragment;

stable adducts are formed through covalent bonds with Hb;

no typical highly polymeric "cross-linking products" are formed under the selected reaction conditions;

the stability against oxidation in terms of methemoglobin formation is enhanced as compared to that of hemoglobin;

the hemoglobin-heparin fragment adducts may be prepared by reacting oxygenated hemoglobin solutions, or preferably deoxygenated hemoglobin solutions, with the reactive heparin fragments in an aqueous solution of a buffer in the pH range of from 5.5 to 8.5. In a consecutive step the possible excess of heparin fragments is removed by means of an ultrafiltration process (diafiltration) and at the same time the buffer medium readjusted with Tyrode buffer or a dialysis buffer.

Another surprising field of application of heparin fragments (prepared in accordance with the known processes) was incidentally found, when the incubation was carried out with intact erythrocytes, instead of hemoglobin solutions, at room temperature in an isotonic BISTRIS buffer, pH 7.4. Simple mixing of the heparin fragments in isotonic solution with erythrocytes at a molar ratio of hemoglobin tetramer to heparin fragment varied from 1:0.5 to 1:20 resulted in an increase of the P 50 value of the erythrocytes up to 9.31 kPa (70 mmHg). Hemolysis of the erythrocytes could not be determined under these conditions. Also after inclusion of the heparin fragment prepared according to Example 1 with DMSO according to the method of Franco and Weiner (U.S. Pat. No. 4,478,824) or after incorporation of the heparin fragment in liposomes and incubation with erythrocytes (EP 0 052 322) or also by the method described by M. Chaissaigne et al. always an introduction of the heparin fragment into the erythrocytes—measured by the increase in the P 50 value —could be accomplished. The heparin fragments used according to the invention are suitable for being introduced into erythrocytes and therein cause an increase in the P 50 value. Even after four weeks of storage of the erythrocyte suspensions thus treated a permanently high P 50 value was measured, so that these heparin fragments apparently are not decomposed in erythrocytes.

Of course, hemoglobins having an increased P 50 value may also be subjected to further consecutive steps such as the inclusion in hemosomes or, if required, a conventional cross-linking with conventional bi- or polyfunctional crosslinking agents such as glutardialdehyde.

Although the P 50 value decreases—in a similar way as in the case of a pyridoxalated hemoglobin—as compared to that of an uncross-linked hemoglobin-heparin fragment adduct, it is still within the range of P 50 values calculated as being the optimum.

Usually the heparin fragments are reacted with hemoglobin solutions in an aqueous solution in a pH range of from 5.5 to 8.5, and preferably from 6.1 to 7.8. The concentration of the hemoglobin solution is between 0.5 and 40% by weight, and preferably at from 5 to 9% by weight, of hemoglobin tetramer. Suitable buffers are, for example, phosphate buffers, hydrogencarbonate buffers or BISTRIS buffers. The concentration of buffering ions is in the range of from 0.05 to 1M. The reaction temperature may be selected from within the range of from 2° C. to 60° C., while the mildest reaction should be effected between 10° C. and 30° C. The possibility of increasing the reaction temperature up to 60° C. does already indicate the high thermal stability of the hemoglobin-heparin fragment adducts. However, usually and preferably the modifying reaction with the heparin fragments is carried out at room temperature.

The modifying reaction is preferred to be carried out under anaerobic conditions in a laboratory fermenter. Laboratory fermenters are particularly well suitable for the reaction of hemoglobin with heparin fragments, because they allow operation under sterile conditions;

the equipment provides facilities for monitoring the temperature, pH value, $O_2$ saturation and redox potential;

stirrer may be inserted;

the composition of the material in the gas volume is checked and controlled (purging with inert gas such as $N_2$);

it is possible to supply buffer and reagent solution under sterile conditions;

it is possible to take samples under sterile conditions;

it is possible to control the temperature.

The methods for deoxygenating solutions containing hemoglobin are known to the artisan.

Three different process variants were chosen:

(a) Passing nitrogen through the system;

(b) Blowing hydrogen into the system in the presence of suitable catalysts;

(c) Deoxygenation using microporous hollow fibers [R. Schmukler, Shu Chien; "Biorheology" 22, 21–29 (1985) "Rapid Deoxygenation of Red Cells and Hemoglobin Solution using Hollow Capillary Fibers"].

For carrying out the process variant (b) in the hemoglobin solution noble metal catalysts such as, for example, Lewatit OC 1045 (Bayer AG, Leverkusen, West-Germany) are suspended. After introducing hydrogen gas the oxygen bonded to hemoglobin and the dissolved oxygen is removed according to $2 H_2 + O_2 \rightleftharpoons 2 H_2O$. At all events the oxygen saturation is less than 0.05% of $O_2$. After the oxygen has been removed from the hemoglobin solution with monitoring the $O_2$ partial pressure, the heparin fragment dissolved in buffer is dropwise added under sterile conditions. The progress with time of the modifying reaction can be watched by applying a sample of the reaction mixture onto a cation exchanger (Mono S, Pharmacia). A reaction time of five hours at room temperature is usually sufficient.

The ratio of hemoglobin to heparin fragment determines the properties (P 50 value) of the reaction product. As the reference standard for hemoglobin there is always used the hemoglobin tetramer having the molecular weight of 64,500. The molar ratios of Hb/heparin fragment usually are between 1:0.4 to 1:5, and preferably between about 1:3 to 1:5. Since the molecular weight of the heparin fragment is not uniform, but the heparin fragment, as heparin itself, exhibits a molecular weight distribution, only average molecular weights of the fragment (about 2,000 D) may be used in calculations. Thus, for the sake of simplification, a mass ratio of heparin fragment/Hb of from 1:7 to 1:84 was chosen, if heparin fragments having a molecular weight of 2,000 D are employed. A different reference standard for heparin fragments cleft using $HNO_2$ is the aldehyde content which is determined by a photometric test using MBTH as a reagent and formaldehyde as comparative standard. The selected molar ratio corresponds to a ratio (Hb)/(aldehyde content of the heparin fragment) of 1:0.4 to 1:5 (at an average aldehyde content of 0.5 $\mu$mol/mg of heparin fragment).

In some cases a reduction with sodium borohydride was subsequently carried out. An excess of $NaBH_4$ in aqueous solution was dropwise added in a molar ratio of 1:20, based on hemoglobin, and the mixture was stirred at room temperature for another 10 hours. However, as a rule this step was omitted, because the heparin fragments produced by $HNO_2$ degradation are stably linked to hemoglobin.

In a further process variant the adduct of hemoglobin and heparin fragment was subjected to conventional cross-linking with glutardialdehyde. This reaction is also preferred to be carried out in the absence of oxygen.

A 10% solution of glutardialdehyde was dropwise added in a molar ratio of Hb/glutardialdehyde in the range of from 1:3 to 1:7. The pH value is about 6.6. After a reaction time at 25° C. of 1 hour the cross-linking reaction was terminated by addition of a ten-fold molar excess of glycine (based on the amount of glutardialdehyde employed), and after a reaction period of 3 hours the reaction mixture was worked up as usual.

In the work-up of the reaction mixture, first the hemoglobin concentration in the fermenter vessel was adjusted to 5 to 7% (conforming to 50 to 70 mg of Hb tetramer per 1 ml of solution), and diafiltration is carried out against a buffer, e.g. Tyrode's buffer.

The ultrafiltration membranes used for the diafiltration, for example, MWCO 10000 D of the firm Millipore (Pellicon-System) were operated under transmembrane pressures of up to 4 bar to allow a rapid volume exchange to be achieved. For the full separation of the reactants and reagents from hemoglobin the liquid volume was exchanged at least fife times.

Usually, Tyrode's buffer was used which contains 0.8 g of NaCl, 0.02 g of KCl, 0.02 g of $CaCl_2$, 0.01 g of $MgCl_2 \cdot 6H_2O$, 0.005 g of $NaH_2PO_4$, 0.1 g of $NaHCO_3$ and 0.1 g of glucose in 100 ml of solution. If required, the pH value was adjusted with NaOH or HCl to pH 7.4 at 37° C.

In the ultrafiltrate the concentration of the heparin fragment was checked by means of the photometric test using toluidine blue. Unexpectedly, the coupling yield, based on the amount of heparin fragment employed in the reaction, always was between 96 and 99.5%.

For sterile filtration and removal of possibly present pyrogens the modified hemoglobin solution was filtered through a 0.2 $\mu$m filter candle having a positive zeta potential and filled into sterile glass bottles.

The following analytical methods can be used for characterizing the obtained adducts of hemoglobin to heparin fragment:

1Clotting test (apTT): This test provides information on the presence of stroma components or clotting-active heparin fragments in the final product.

Determination of the hemoglobin concentration.
Ion exchange chromatography through Mono S (Pharmacia).
Determination of the methemoglobin content.
Determination of the molecular weight of hemoglobin either by an analytical ultracentrifugation or, as a routine operation, by gel permeation chromatography.
SDS gel electrophoresis [according to U.K. Laemmli, Nature 227, 680–685 (1970)].
Determination of the colloid-osmotic pressure.
Determination of the osmolarity.
Measurement of an oxygen binding curve with calculation of the P 50 value and of the Hill coefficient.
Measurement of the viscosity.

As the result of the analytical tests it was shown that neither in the SDS gel electrophoresis nor by gel permeation chromatography, for example through Superose ® 12 (Pharmacia) an increase of the hemoglobin molecular weight could be measured. Also the analysis of amino acids of an acidic hydrolyzate of the reaction product did not show any alteration in the amino acid pattern when compared to that of un-reacted hemoglobin.

However, a reaction can be clearly proven by the following criteria:

Ion exchange chromatography through a cation exchanger Mono S (Pharmacia). In the course of the progress of the reaction a further signal group is detectable in the elution profile which is detected at shorter retention times than HbA (cf. FIG. 5).

Separation of the hemoglobin-heparin fragment adducts by means of RP chromatography, for example FPLC Pharmacia, type Pro RPC HR 5/10: This separation shows a shift in the retention time of the $\alpha$- and/or $\beta$-chain as compared to unmodified hemoglobin.

Oxygen binding curve: The Hill coefficient is lowered at high degrees of conversion to values of about 1.0. The P 50 value is increased, and more specifically so at a molar ratio of hemoglobin/heparin fragment of 1:5, to values around 7.99 kPa (60 mmHg).

If the reaction mixture of hemoglobin and heparin fragment is subjected to an ultrafiltration using a membrane impermeable to hemoglobin, but permeable to heparin fragments, then free heparin fragment is detectable in the ultrafiltrate. After completion of the modifying reaction, only traces of heparin fragments are detected in the ultrafiltrate. Therefrom a coupling yield of more than 96%, based on the heparin concentration as initially employed, can be calculated.

Independently of these physico-chemical criteria the intravasal half-life time in dog upon intravenous administration of the sterile pyrogen-free hemoglobin-heparin fragment adduct prepared according Example 1 was 10 hours. In comparison thereto, the control value of a pure stroma-free unmodified hemoglobin solution was only 2 hours. In both cases the dose, based on the body weight, was 750 mg/kg of hemoglobin.

In the course of further investigations it could be shown that other glycosaminoglycan fragments having reactive terminal groups may be used for modifying hemoglobin in the same manner as heparin fragments. For example, chitosan was first deacetylated in the acidic pH range, sulfated by means of known procedures and like heparin reacted with $HNO_2$ at pH 4.0 for degradation. In this reaction sequence there could also be obtained sulfated glycan moieties which can be reacted with hemoglobin to increase the P 50 value.

The hemoglobin-heparin fragment adducts exhibit an unusually high thermal stability. Thus, for example, it was possible to heat the composition prepared according to Example 1 at 60° C. for 10 hours without formation of any water-insoluble precipitate. Pre-requisite therefor was that the composition was present in the deoxygenated form. Deoxygenation was effected by anyone of the two steps as described, namely by supplying nitrogen and/or introducing hydrogen in the presence of a (noble metal) catalyst. It could further be shown that the hemoglobin-heparin fragment adducts can be lyophilized upon addition of skeleton-forming materials such as glycine, sorbitol and glucose. In this process step the methemoglobin increased to values around 4.5%.

Influence of the Variation of the P 50 Value on Various Parameters of the $O_2$-Transportation By means of a computer program combined with the device for determining the oxygen binding curves [see Gersonde (1985) loc. cit., W. Gauch, Dissertation RWTH Aachen, West-Germany, 1986] it is possible with the measured P 50 values to simulate $O_2$ transportation parameters such as the arteriovenous difference, the amount of $O_2$ available and the amount of $O_2$ consumed, based on the assumption of the following parameter values: $P_aO_2 = 12.63$ kPa (95 mmHg), $P_vO_2 = 5.32$ kPa (40 mmHg), a heart volume per minute of 4,700 ml/min, a Hb concentration of 6.7%, a dead space breath air per time (VT) of 5,600 ml/min, a dead space (VD) of 10% and an $O_2$ content of 21%

Table 1 shows the advantage of the increased P 50 value of a modified hemoglobin over an unmodified hemoglobin solution: The increase as found of the arterio-venous concentration difference signifies an enhanced exhaustion of the oxygen bound to hemoglobin by the factor of 2.1 (see Table 1).

TABLE 1

Arterio-venous difference $avDO_2$ for normal and rightwardly shifted $O_2$ binding curves

| P 50 kPa (mmHg) | $P_aO_2$ kPa (mmHg) | $P_vO_2$ kPa (mmHg) | $C_aO_2$ (ml $O_2$/ml) | $C_vO_2$ (ml $O_2$/ml) | $avDO_2$ (ml $O_2$/ml) |
|---|---|---|---|---|---|
| 1.51 (11.39) | 12.63 (95) | 5.32 (40) | 0.0880 | 0.0772 | 0.0107 |
| 7.07 (53.16) | 12.63 (95) | 5.32 (40) | 0.0618 | 0.0393 | 0.0225 |

Notes:
$P_aO_2$ = arterial oxygen partial pressure;
$P_vO_2$ = venous oxygen partial pressure;
$C_aO_2$ = arterial $O_2$ concentration;
$C_vO_2$ = venous $O_2$ concentration;
$avDO_2$ = arterio-venous oxygen concentration difference.

The attached Figures as mentioned below show the following items:

FIG. 1: Oxygen binding curves of solutions containing hemoglobin: 1A shows modified hemoglobin, 1B shows unmodified hemoglobin.

Figure 2:
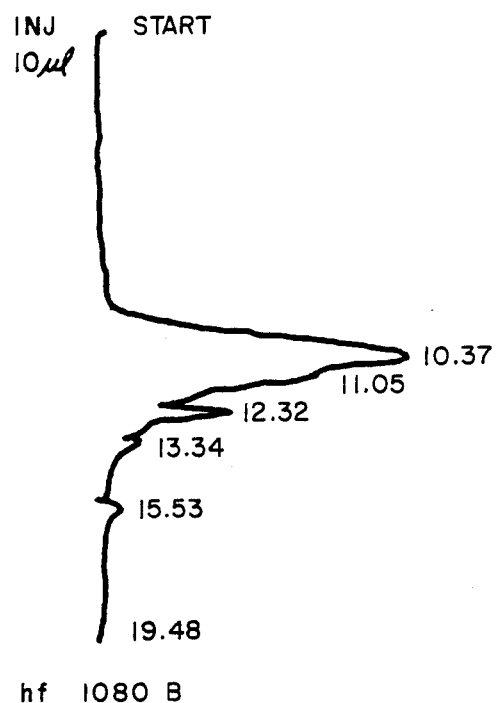

FIG. 2: Elution profile of the heparin fragment prepared according to 1.1. The retention time of the peak maximum is 10.37 minutes.

Figure 3:
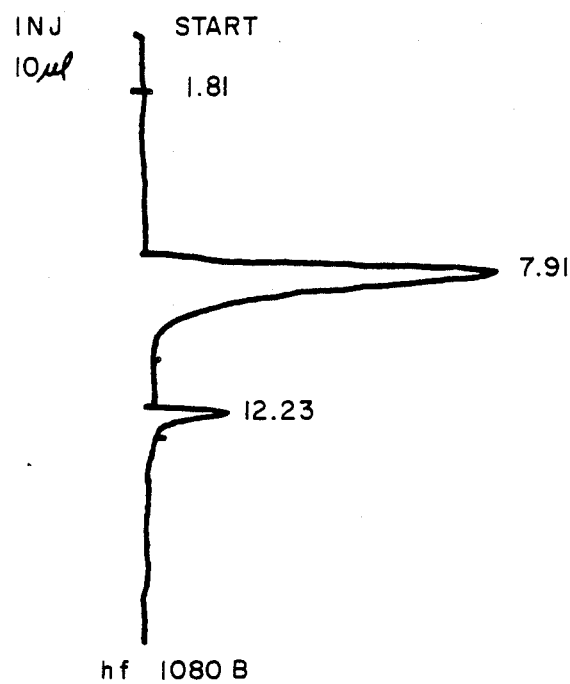

FIG. 3: Elution profile of a commercially available heparin sodium salt. The retention time of the peak maximum is 7.91 minutes.

Figure 4:
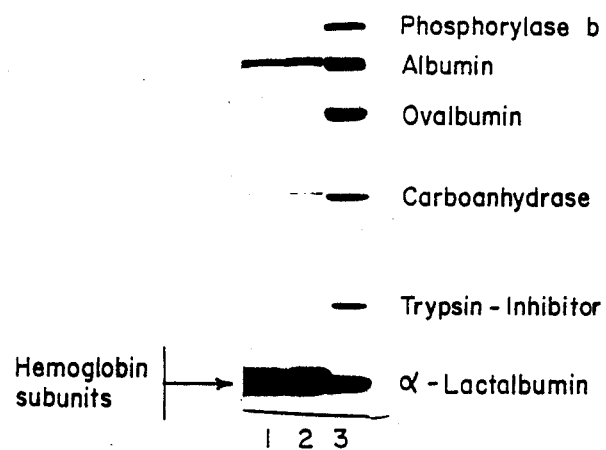

FIG. 4: SDS polyacrylamide gel electrophoresis. Path 1: Hb lysate, untreated; Path 2: Hb preparation, reacted with heparin fragment according to Example 1.1; Path 3: Molecular weight markers (Phosphorylase b-94,000 D; Albumin-67,000 D; Ovalbumin-43,000 D Carboanhydrase-30,000 D; Trypsin-Inhibitor-20,100 D; α-Lactalbumin-14,400 D).

Figure 5B:
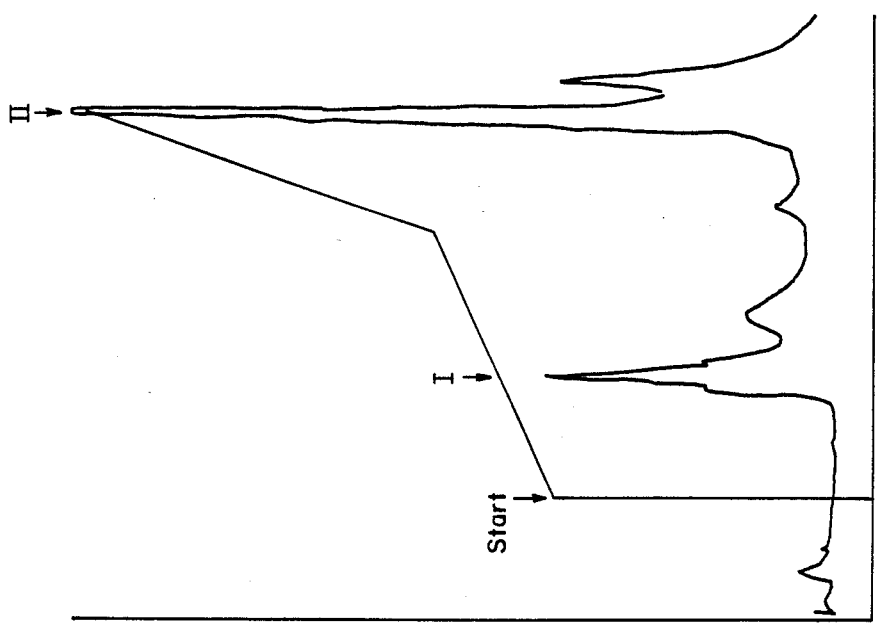
Figure 5A:
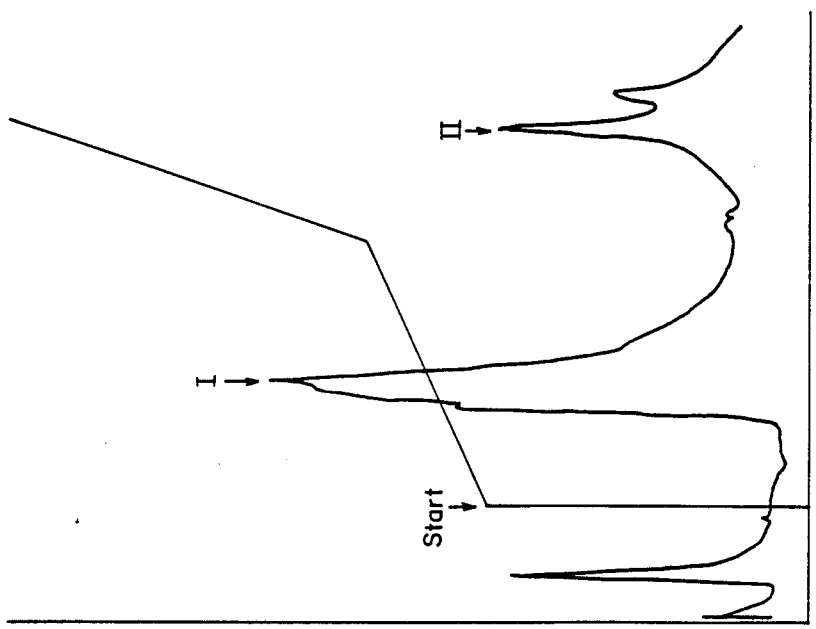

FIG. 5: Ion exchange chromatography through FPLC Mono S: 1A) Hb lysate, treated with heparin fragment, 1B) native Hb lysate, untreated.

Figure 6A:
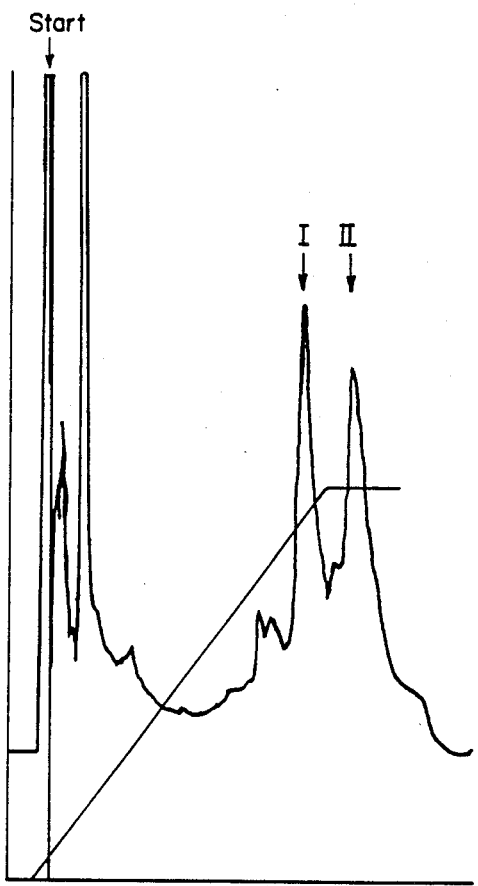
Figure 6B:
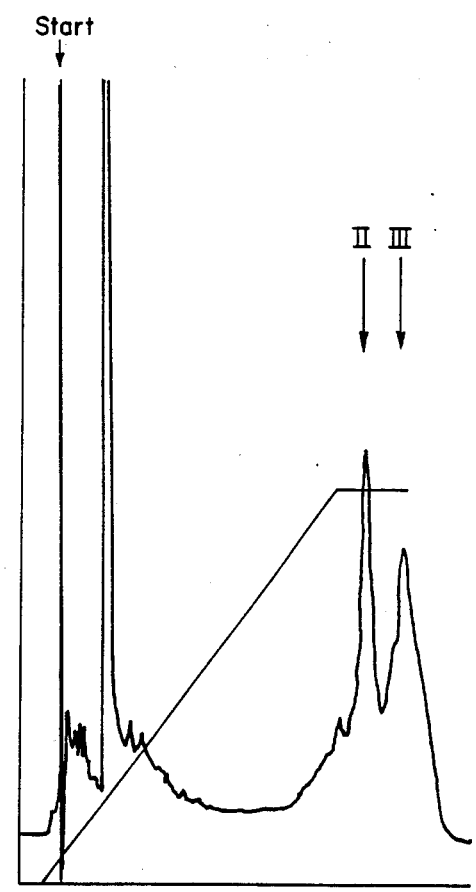

FIG. 6: FPLC Reversed-phase chromatography: (1A) Control: Hb lysate, native, (1B) Cross-linked Hb preparation.

FIG. 7: $O_2$ binding curves: (7B) untreated Hb lysate: P 50 = 6.42 mm Hg; N = 2.25, (7B) Hb preparation (prepared according to 1.3): P 50 = 62.98 mm Hg; N = 1.07

Figure 8:
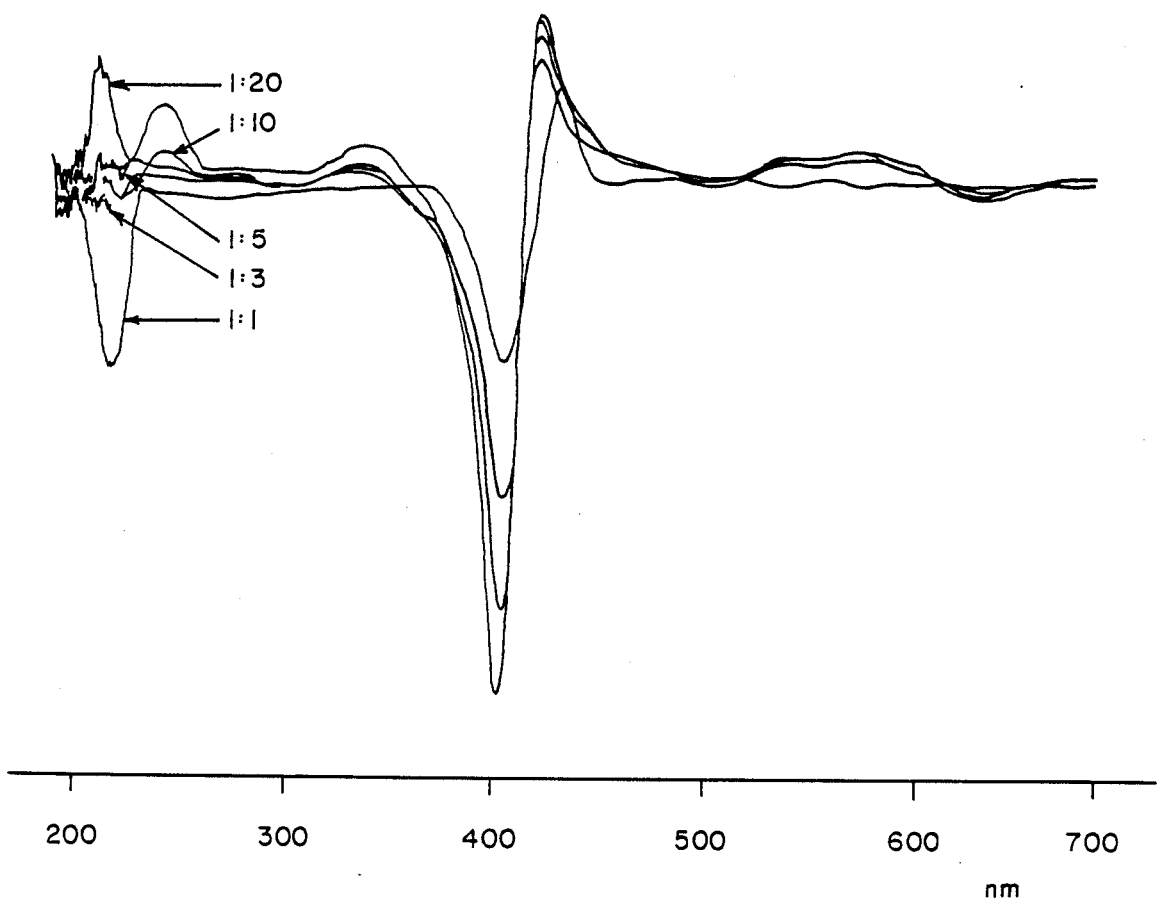
Figure 8:
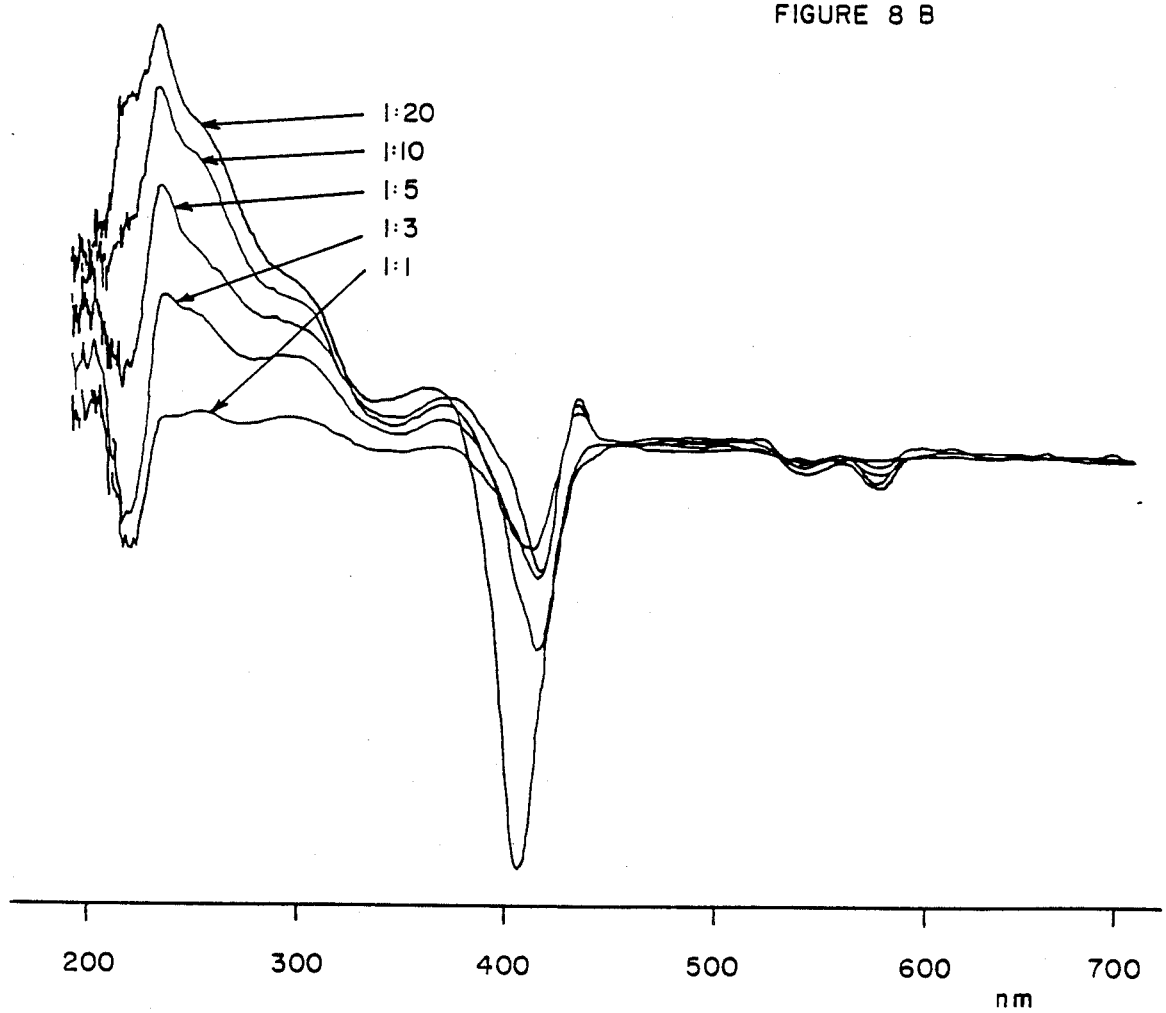

FIG. 8 A: UV-VIS Spectrum (hemoglobin + inositol hexaphosphate)

FIG. 8 B: UV-VIS Spectrum (hemoglobin + heparin fragment)

Figure 9:
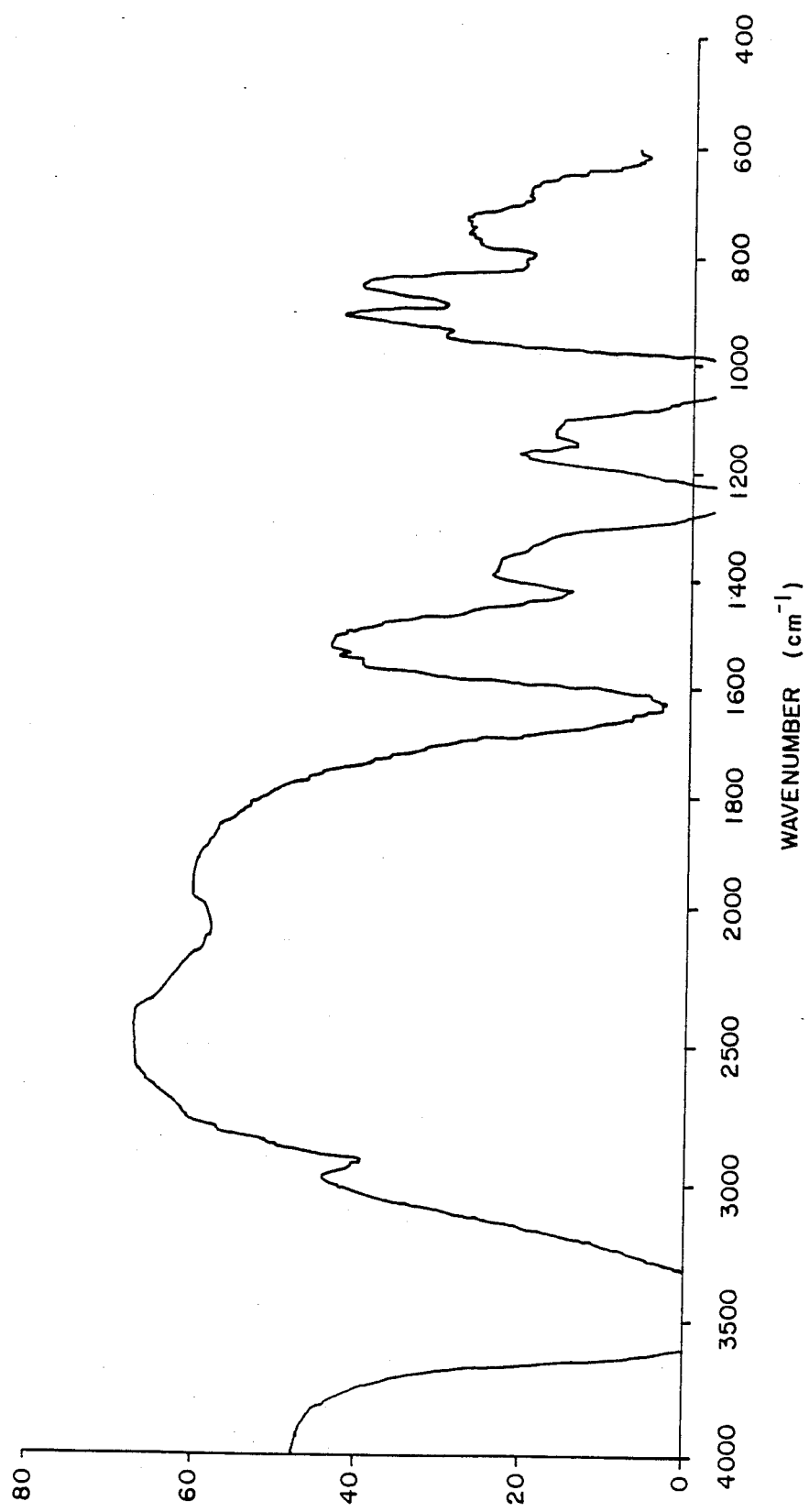
Figure 9:
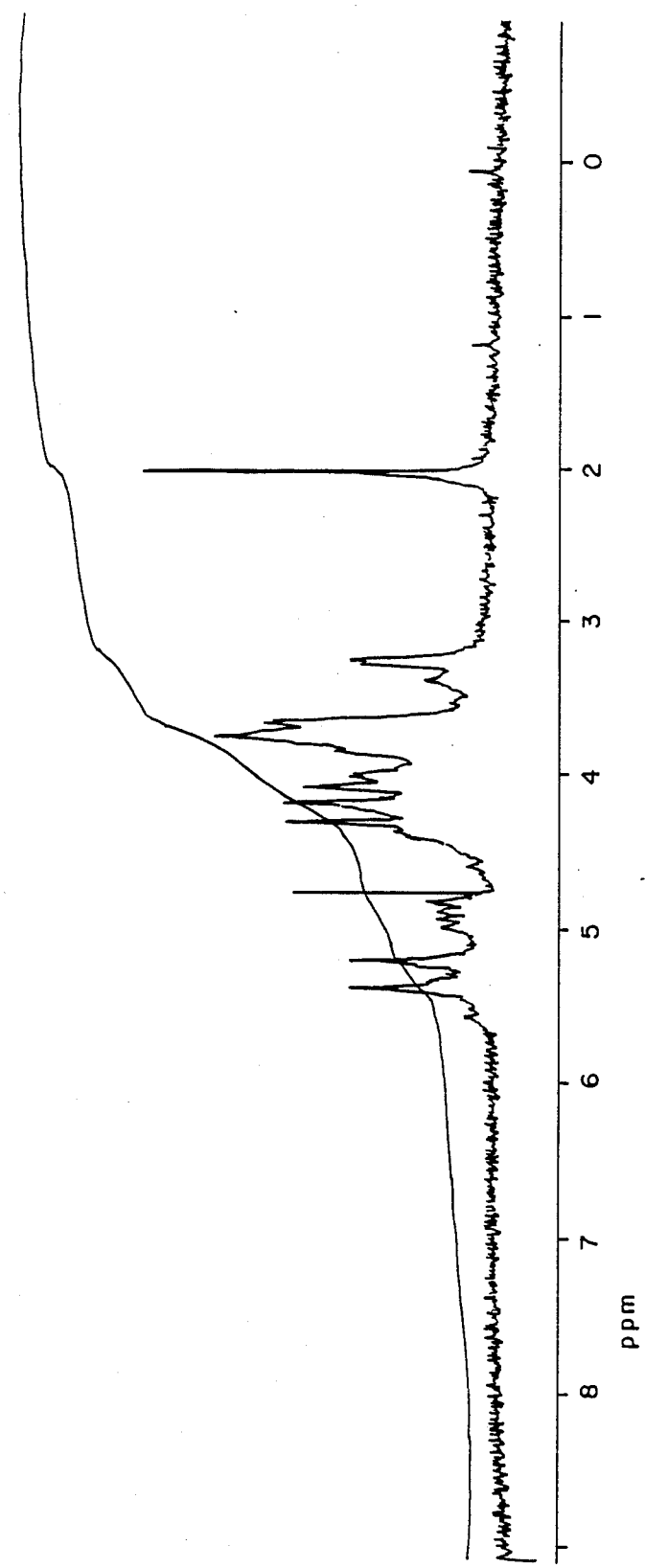
Figure 9:
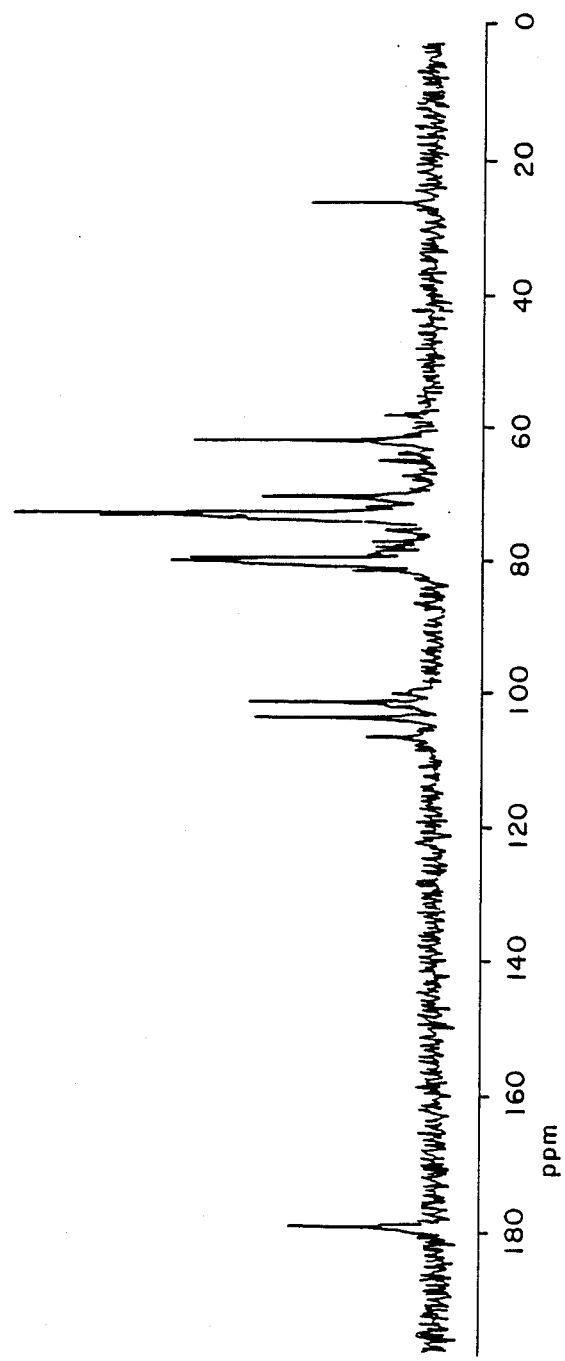

FIG. 9 A: IR Spectrum of an unfractionated heparin

FIG. 9 B: $^1$H-NMR Spectrum of an unfractionated heparin

FIG. 9 C: $^{13}$C-NMR Spectrum of an unfractionated heparin

Figure 10:
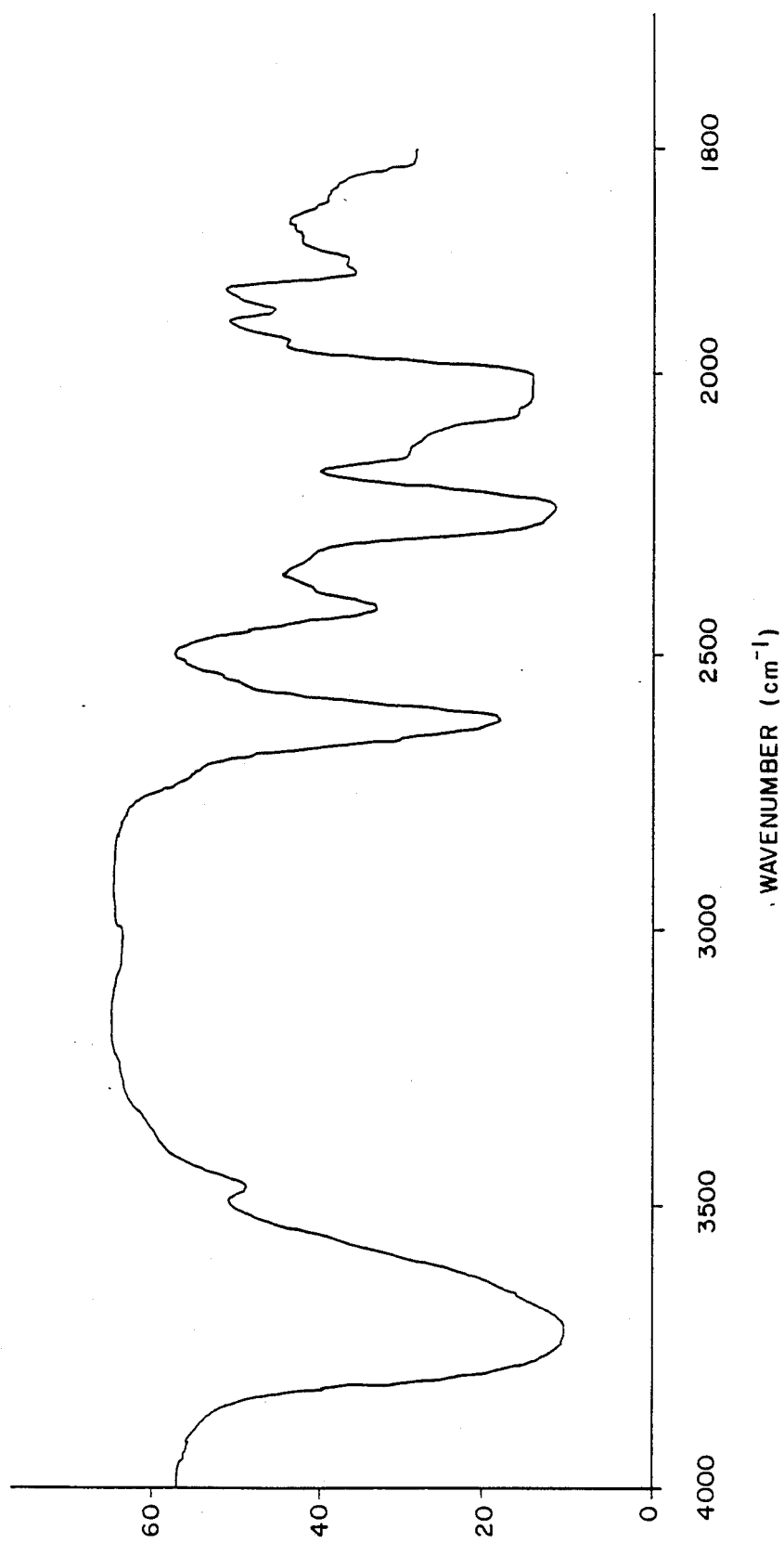
Figure 10:
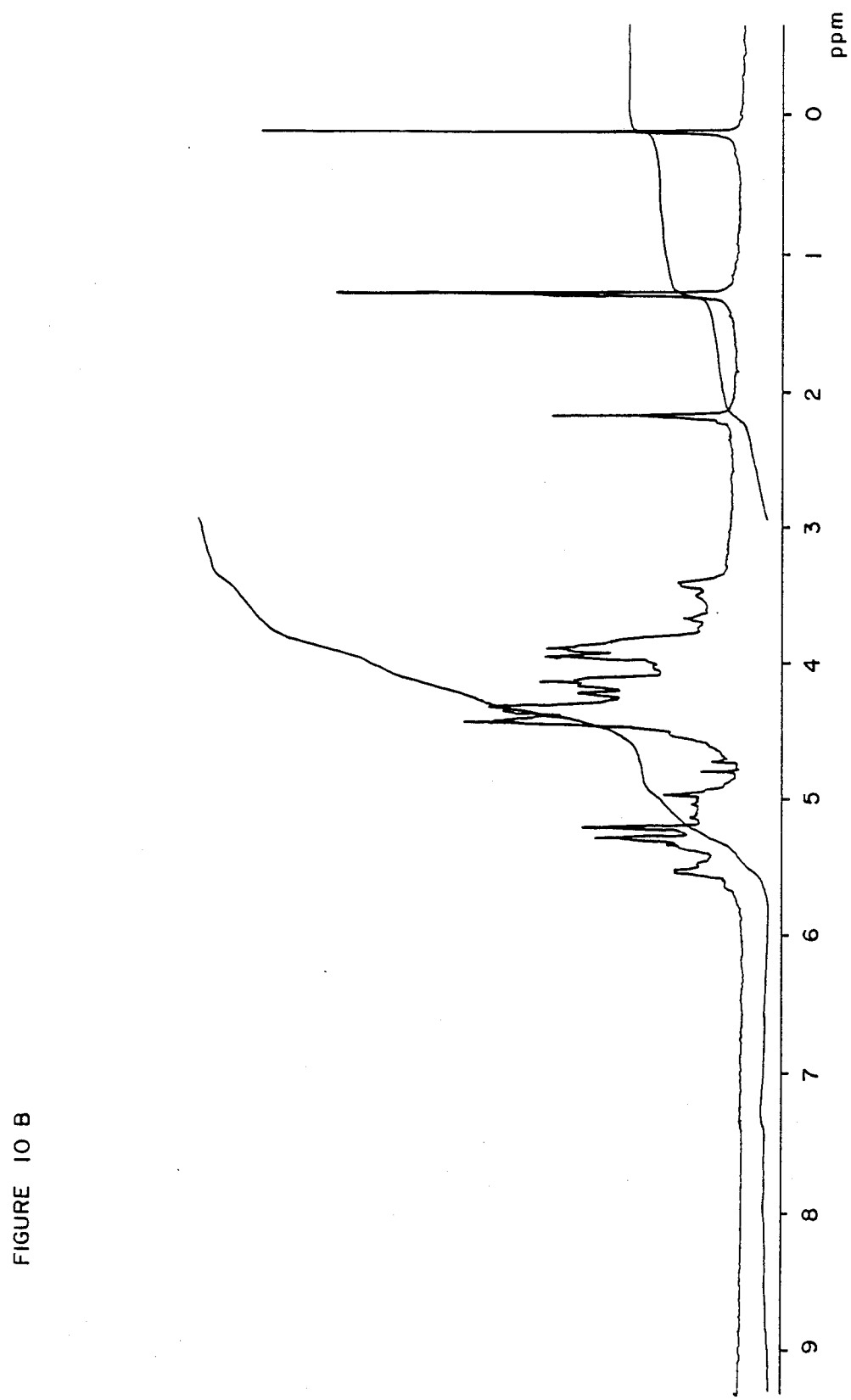
Figure 10:
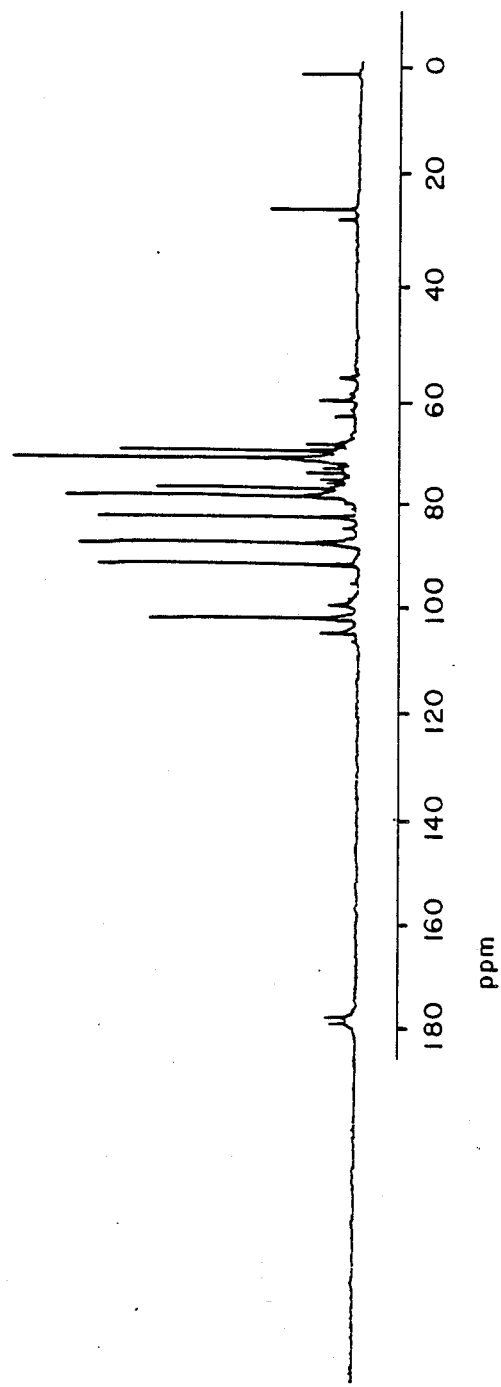

FIG. 10 A: IR Spectrum of a heparin fragment prepared according to Example 1

FIG. 10 B: $^1$H-NMR Spectrum of a heparin fragment prepared according to Example 1

FIG. 10 C: $^{13}$C-NMR Spectrum of a heparin fragment prepared according to Example 1

Figure 11A:
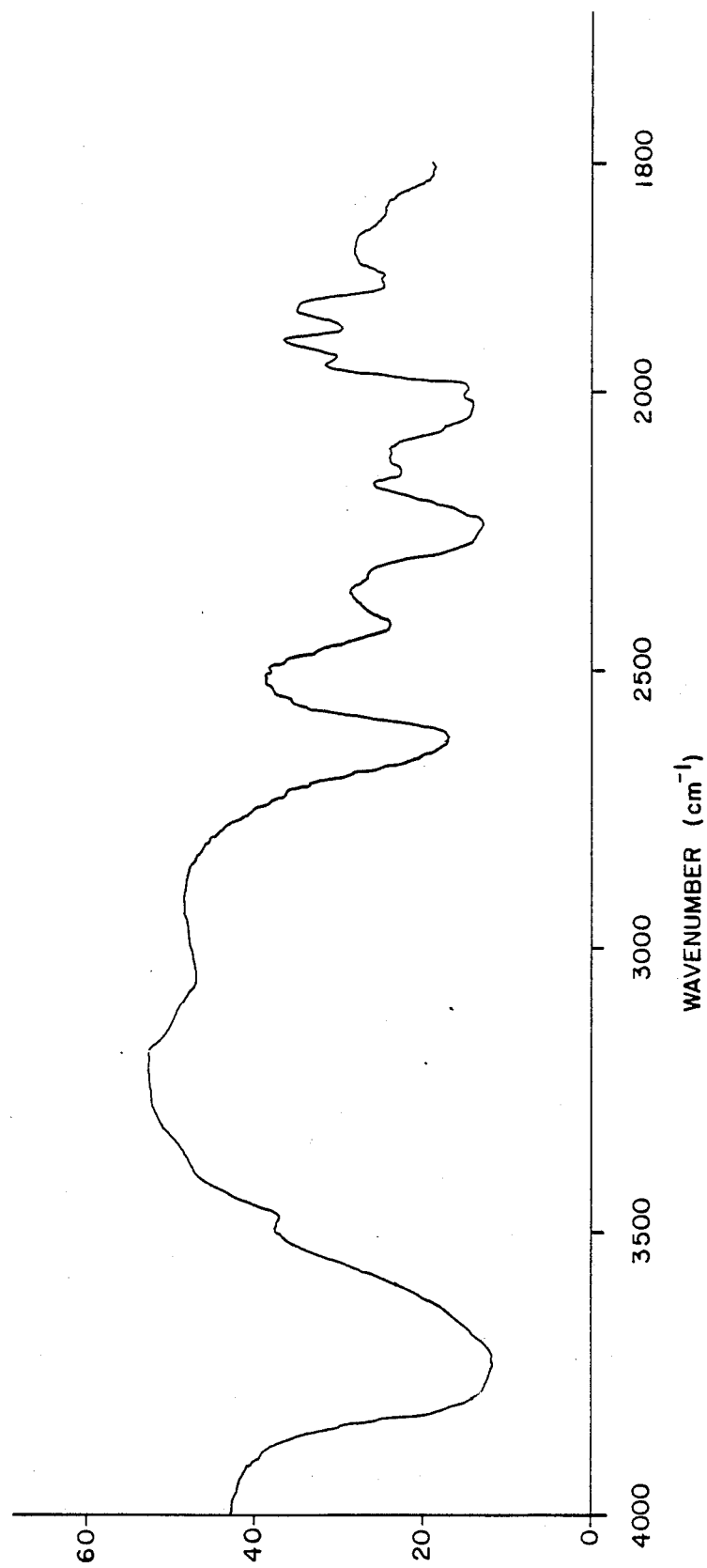

FIG. 11 A: IR Spectrum of a heparin fragment prepared according to Example 2

FIG. 11 B: $^1$H-NMR Spectrum of a heparin fragment prepared according to Example 2

FIG. 11 C: $^{13}$C-NMR Spectrum of a heparin fragment prepared according to Example 2

Figure 12:
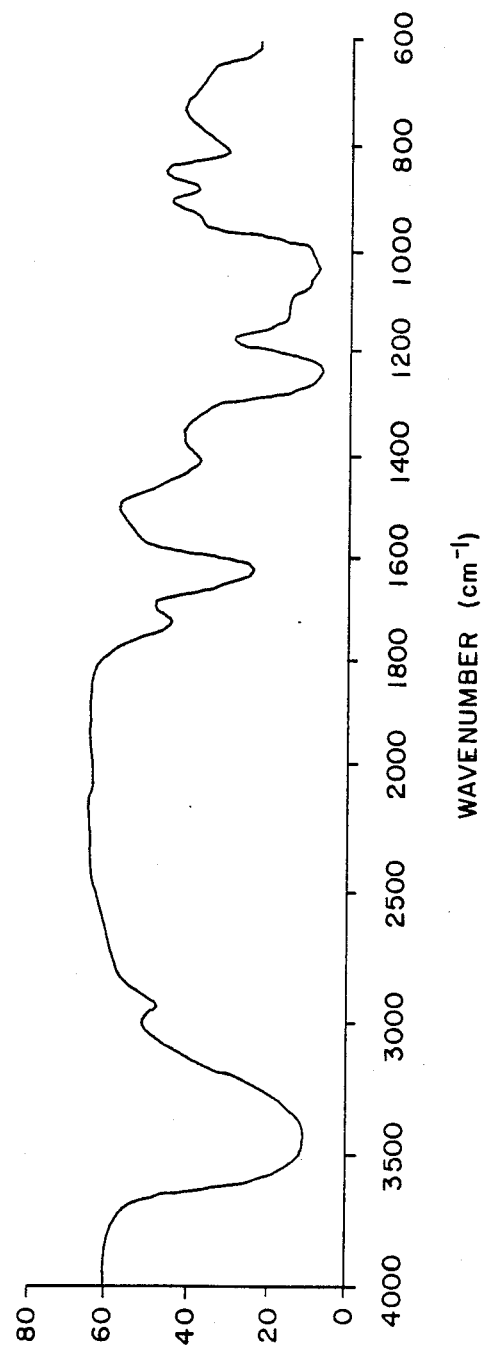
Figure 12:
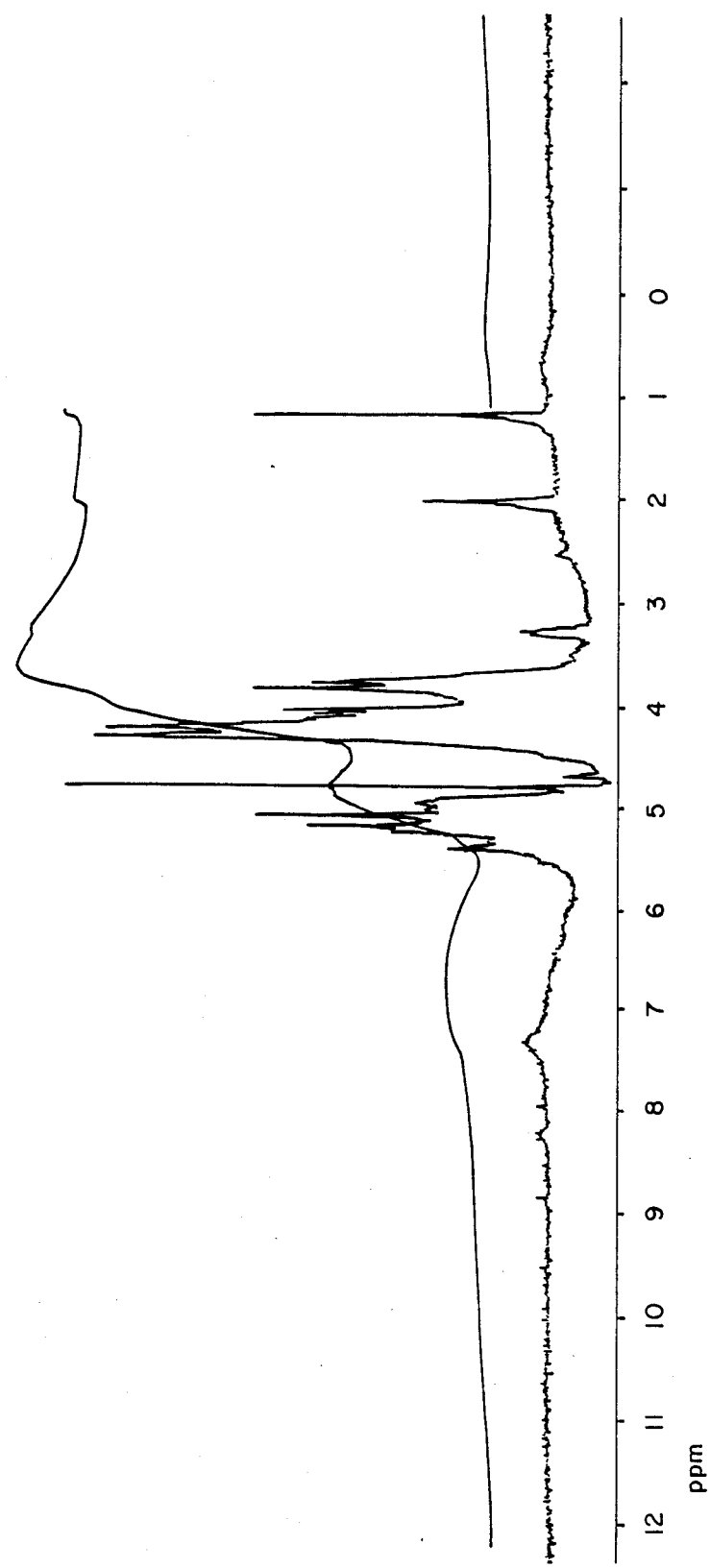
Figure 12:
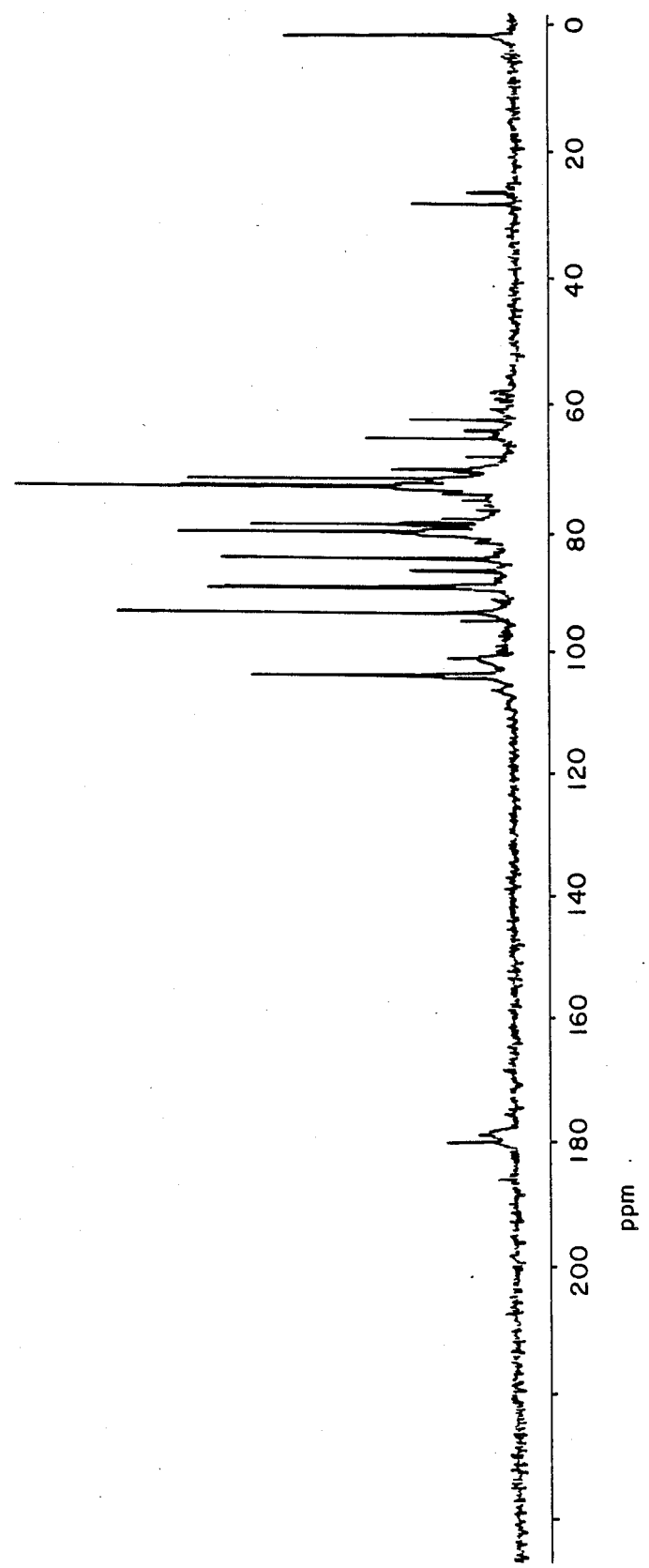

FIG. 12 A: IR Spectrum of a heparin fragment prepared according to Example 3

FIG. 12 B: $^1$H-NMR Spectrum of a heparin fragment prepared according to Example 3

FIG. 12 C: $^{13}$C-NMR Spectrum of a heparin fragment prepared according to Example 3.

Influence of the Variation of the Ratio Hemoglobin/Heparin Fragment on the P 50 Value As is shown by the Examples 1 to 7, fragments of heparin or heparin-like starting materials of various origin are suitable for increasing the P 50 value after covalent coupling to Hb.

The degree of the rightward shift of the $O_2$ dissociation curve of hemoglobin at constant molecular weight and aldehyde content of a heparin fragment depends also on the ratio of Hb/heparin fragment.

The following investigations—conducted using two different heparin fragments—furnish evidence of that the P 50 can be varied within a wide range only by adjusting the ratio of Hb/heparin fragment:

In each of separate batches 1 ml of deoxygenated hemoglobin lysate (concentration 6.7% of HbA) was incubated with increasing amounts of heparin fragment (4 hours, room temperature), the hemoglobin-heparin fragment adduct was separated from remainders of free heparin fragment and desalted by chromatography through a Sephadex G 75 column equilibrated with BISTRIS-Puffer (pH 7.4) and re-concentrated to a hemoglobin content of 6%, and the P 50 value thereof was determined at 37° C.

The obtained results are shown in the following Table:

| Amount of heparin fragment in the Hb solution | P 50 of fragment of Example 1 | | P 50 of fragment of Example 3 | |
|---|---|---|---|---|
| mg/ml | kPa | (mm Hg) | kPa | (mm Hg) |
| 0.2 | 1.61 | (12.1) | 1.50 | (11.3) |
| 0.8 | 4.28 | (32.2) | 2.87 | (21.6) |
| 2.0 | 4.20 | (31.6) | 3.27 | (24.6) |
| 3.0 | 4.92 | (37.0) | 4.31 | (32.4) |
| 4.0 | 5.36 | (40.3) | 5.08 | (38.2) |
| 10.0 | 8.291 | (62.34) | 9.31 | (70.0) |

UV/VIS Spectroscopic Documentation of the Influence of the

Heparin Fragment on the Hemoglobin Structure

The following experiment was carried out in order to examine whether a heparin fragment causes changes in the hemoglobin structure, which are detectable as changes in the spectroscopic behavior in the UV/VIS spectrum, already upon being mixed with hemoglobin solutions. Inositol hexaphosphate which is ionically bonded to hemoglobin with a high bonding constant and when mixed with hemoglobin shifts the P 50 value towards high oxygen partial pressures was employed as a (positive) control.

Hemoglobin solutions in buffer (50 mM of sodium phosphate, pH 6.8) were mixed with heparin fragments in increasing amounts and in separate experiments with inositol hexaphosphate, respectively, and the spectra of the mixtures were recorded in the spectral range of from 190 to 700 nm. In all cases the hemoglobin concentration was 0.1 mg/ml. The selected molar ratios for Hb/heparin fragment and Hb/inositol hexaphosphate were 1:1, 1:3, 1:5, 1:10 and 1:20. Hemoglobin solution (0.1 mg/ml) was used as reference. The results are shown in FIGS. 8A and 8B.

As a result there is to be noted that an intensive decrease in the extinction at 400 nm is to be observed with both heparin fragment and inositol hexaphosphate which decrease is dependent on the concentrations of the added substances. The UV/VIS spectra of heparin and inositol hexaphosphate, respectively, do not exhibit any absorption in the 400 nm region.

EXAMPLES

Example 1

1.1 Preparation of a lower molecular weight heparin fragment from heparin sodium by degradation with $HNO_2$ Fifty grams of commercially available heparin sodium salt from porcine mucosa are dissolved in 1 liter of 0.05M sodium acetate buffer, pH 4.0. The fragmentation reaction is initiated by the addition of 400 ml of a 4% by weight sodium nitrite solution and is maintained under a fume hood at 25° C. for 24 hours. Then the reaction mixture is neutralized to pH 7.0 with a 5% NaOH solution. The molar ratio of heparin (MW 13,000) and sodium nitrite in this heparin dergradation is 1:67.

For further work-up the mixture is dialyzed in a Cuprophan dialysis tube against water until nitrite ions are no longer detectable in the dialyzate. The "Merck-Aquaquant" system is employed in the test for nitrite. At the same time it is checked whether, and if so, how much of heparin fragment in the dialyzate passes through the dialysis membrane. The dialysis is terminated as soon as nitrite is no longer detectable in the dialyzate.

Larger batches are diafilterated using a Millipore ultrafiltration membrane having a cut-off value of 1,000 D. After the dialysis or diafiltration of the reaction product the material is either lyophilized, or the solid substance is isolated by spray-drying. The yield is about 70%.

The heparin concentration in the dialyzate or ultrafiltrate is determined by mixing 100 μl of a sample solution with 2.5 ml of a reagent solution (20.0 mg of toluidine blue/1000 ml) and measuring the extinction at 623 nm against the reagent blank value. The results are evaluated by comparison to a calibration curve established in the same manner. This photometric method is described in: Paday, J. F. "Chemistry and Molecular Biology of the Intercellular Matrix" Vol. 2, Ed.: E. A. Ballazs, Academic Press 1970, page 1007–1031 and by Silbert, Biochem. Biophys. Res. Commun. 69, pp. 70 et seq. (1976).

1.2 Characterization of the heparin fragment

The determination of the aldehyde content of the fragment gave 0.52 μmol/mg.

Method:

The aldehyde content is determined according to the method described by B. Kakac and Z. J. Vejdelek, "Handbuch der photometrischen Analyse organischer Verbindungen", Vol. 1, page 233, Verlag Chemie, using MBTH (3-methyl-2-benzothiazolinone hydrazone hydrochloride). Formaldehyde solutions are used as calibrating standard.

Optical rotation: +45.5°

Osmolarity of a 5% solution: 195 mOsm

Spectra $^{13}C$, $^1H$ in comparison to commercially available heparin see FIGS. 9 and 10

Clotting activity: 0.6 U/mg (U.S.P. XX)

Distribution of molecular mass: 1,500 D to 2,500 D

Average molecular weight: 2,000 D.

The molecular mass distribution was determined by gel permeation chromatography on columns packed with Bondagel E 125 and E linear (Company Waters, Konigstein, West-Germany).

HPLC apparatus: HP 1084 (Hewlett-Packard)

Sample concentration 1 mg/ml

Sample volume: 10 μl

Eluant: 0.1M $Na_2HPO_4$ (pH 5.0)/$H_2O$=30:70

Flow: 0.5 ml/min

Detector: UV, measurement at wave length: 205 nm.

FIG. 2 shows an elution diagram of the GPC separation in comparison to that of an unfragmented commercially available heparin (FIG. 3). The molecular weight of the peak maximum is 2,000, while the molecular weight of the unfragmented heparin is 13,000. The molecular weight is read from a calibration curve established by using heparin fractions having known molecular weights.

Noteworthy is the very low anticoagulative activity of the heparin fragments, which amounts to 0.6 U/mg, based on the 4th WHO Standard.

1.3 Preparation of a stroma-free hemoglobin solution

From 15 bags (500 ml) of human erythrocyte concentrate (blood bank) there were obtained after deep freezing at −20° C. and re-liquefaction about 5 liters of lysate which were diluted with 15 liters of water a.i.

The pH value of the solution was adjusted to 5.5 using 0.1N HCl (3 liters), and aqua a.i. was added to the solution to make a total volume of 25 liters.

Beginning with this step all filtration and diafiltration steps were carried out at 4° C. For allowing the stroma components to sediment, the solution was allowed to sit at 4° C. for 24 hours to enable a removal of the stroma remainders.

This was followed by a filtration through Sartopure 0.2 μm filter candles. The pH value of the filtrate was then adjusted to 6.8 using 0.1N NaOH (about 4 liters). Then the solution was concentrated to a total volume of 10 liters using the Pellicon cassette system (Millipore; MWCO: 10,000 D).

Now the pH value was adjusted to 6.8, whereafter the solution was filtered through a 0.2 μm filter into a 12 liter fermenter vessel (Hb concentration: 8.7%; volume: 10 liters).

Sterile nitrogen was purged into the solution at room temperature until an oxygen content of at most 0.05% had been attained in the solution (the $O_2$ solubility in water measured at said temperature was defined as 100%) The Met-Hb content was 1.4%.

Now about 5 liters were branched off a control solution and subjected to a diafiltration against 25 liters of a Tyrode's buffer solution purged with $N_2$ ("stroma-free Hb lysate").

The remaining 5 liters of the untreated lysate (Hb concentration 87 mg/ml) are admixed with the heparin fragment according to 1.1 (34 g dissolved in 100 ml of aqua a.i.). Under these conditions the molar ratios of Hb/heparin fragment is 1:2.5. The reaction mixture is stirred and purged with nitrogen at room temperature for 4 hours. Then it is also diafiltrated against 25 liters of an $N_2$-purged Tyrode's buffer solution, filtered through a 0.2 μm filter, and the obtained solution is filled into sterile bottles. This solution is designated as "hemoglobin preparation".

Composition of Tyrode's buffer: 0.8 g of NaCl, 0.02 g of KCl, 0.02 g of $CaCl_2$, 0.005 g of $NaH_2PO_4$, 0.01 g of $MgCl_2 \cdot 6 H_2O$, 0.1 g of $NaHCO_3$, 0.1 g of glucose in 100 ml (pH 7.48).

Characterization of the product according to 1.3

(a) SDS Polyacrylamide electrophoresis

The separation was effected in accordance with the method published by Laemmli, U.K. ["Cleavage of Structural Proteins During the Assembly of the Head of Bacteriphage T4", Nature 227, 680-685 (1980)].

The separation of the hemoglobin-protein complex takes place under denaturing conditions so that—as shown in FIG. 4 more particularly monomeric protein-hemoglobin units (α-globin and β-Globin, MW 16,400 D and MW 15,850 D, respectively) appear in the gel pattern.

As has been mentioned above, upon use of this separating system no differences become apparent between the control lysate and the modified sample. However a slight increase in molecular weight was found by means of the method subsequently described.

(b) Molecular weight determination using analytical ultracentrifugation

By means of the analytical ultracentrifugation (absolute method) the molecular weight of the hemoglobin/heparin adduct was determined to be 68,800 D as compared to 64,500 D of the native hemoglobin.

(c) Ion exchange chromatography on FPLC Mono S

The bonded heparin fragment to a high degree changes the total charge of the hemoglobin tetramer. By means of ion exchange chromatography the change was shown of the elution profile of the hemoglobin solution modified with heparin fragment as compared to that of untreated hemoglobin as was found by chromatography using a cation exchanger (Mono S, Pharmacia).

Method: "Determination of $HASHED_{1c}$ using a monodisperse cation exchanger"; 5th European Congress of Clinical Chemistry, Budapest, Hungary, July 1983, Jeppsson, J.-O., Englund, H., Nylund, V. et al.

The separation is effected by means of gradient elution using a cation exchanger (Mono S, type HR 5/5, Pharmacia Fine Chemicals, Uppsala, Sweden). (Buffer A: 0.01M malonic acid pH 5.7 buffer B: 0.01M malonic acid pH 5.7 comprising 0.3M LiCl). Detection at 405 nm.

FIG. 5 shows the corresponding chromatograms for a Hb preparation treated with heparin effector (a) and a native untreated Hb lysate (b). The applied salt gradient (percentage of buffer B) is also recorded.

The effect of the heparin derivative added is illustrated by the shift of the group which is eluted later in the chromatogram (designated by II in FIG. 5) relative to a peak group (designated by I) eluting already at a lower ion strength. The conversion rate is quantifiable by the integral ratio of the two peak groups (Peak I/-Peak II=72/28). In the case of the control lysate this ratio was determined to be 12/88. Therefrom a conversion rate of 68.2% may be calculated.

(d) "Reversed-phase" chromatography through FPLC

The hemoglobin molecule is separated into its α- and β-subunits. The modification of hemoglobin or its subunits caused by the reaction with the heparin fragment is furnished evidence of by that the signal designated with I in FIG. 6A (of the β-chain) is no longer visible in the modified hemoglobin solution of FIG. 6B. Instead, a new signal III is eluted at a higher reaction time in FIG. 6B which is missing in FIG. 6A.

Method:

"An integrated approach to the analysis of human hemoglobin variants by combining IEF, FPLC and titration curve analysis"; Electrophoresis '83, Walter de Gruyter & Co., Berlin, 1983, Wahlström, L., Nylund. V., Burdett, P. et al.

The employed column (Pharmacia Fine Chemicals AB, Uppsala, Sweden) "Pro RPC HR 5/10" was operated with a gradient of 39% of acetonitrile, 0.3% of trifluoroacetic acid (A) and 45% of acetonitrile, 0.15% of trifluoroacetic acid (B) (detection by measuring the extinction at 280 nm; flow rate: 0.2 ml/min).

(e) Oxygen binding curve ($O_2$ affinity)

Figure 7A:
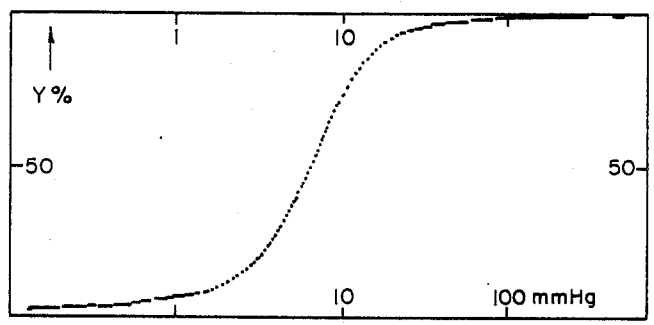
Figure 7B:
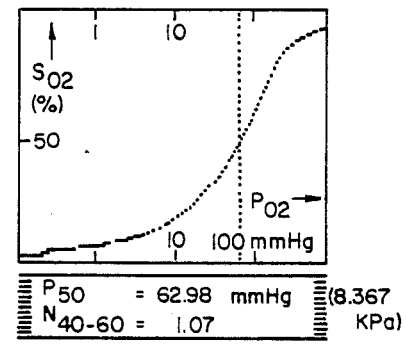

By means of the method developed by Sick, H. and Gersonde, K. ["Continuous Gas-Depletion Technique for Measuring $O_2$-Dissociation Curves of High-Affinity Hemoglobin" Anal. Biochem. 146, 277-280 (1985)]the oxygen binding property of the modified Hb preparation was investigated. In FIG. 7 the obtained results are compared to data obtained with an unmodified Hb lysate:

For the untreated Hb lysate (FIG. 7a, Comparative Example 1) there is found a P 50 of 0.854 kPa and a Hill coefficient (N) of 2.25, while the modified Hb preparation (prepared according to 1.3, FIG. 7b) has a P 50 of 8.367 kPa and a Hill coeffizient of 1.07.

(f) Viscosity: Using a capillary viscosimeter according to Ubbelohde of the Company Schott, Mainz, West-Germany, the viscosity of the modified hemoglobin solution was determined to be 1.45 cSt ($H_2O$: 0.73 cSt; full blood 2.45 cSt; measured at 37° C.).

Comparative Example 1

5 liters of the control solution prepared according to Example 1.3 were branched off and subjected to a diafiltration against 25 liters on an $N_2$-purged Tyrode's buffer solution.

After a sterile and pyrogen filtration through a 0.2 μm filter the solution is directly filled into 500 ml bottles under sterile conditions. This solution is also designated as stroma-free hydrolyzate.

The results of the analytical investigations of the solutions according to Example 1 and to Comparative Example 1 are shown in the following Table:

|  | Hemoglobin preparation Example 1 | Stroma-free Hb lysate of Comparative Example 1 |
| --- | --- | --- |
| Hb A | 9.3% | 7.6% |
| Met-Hb | 3.6% | 3.4% |
| Pyrogen test | Endotoxin-free | Endotoxin-free |
| P 50 | 8.376 kPa (62.98 mm Hg) | 0.854 kPa (6.42 mm Hg) |
| pH value (37° C.) | 7.4 | 7.4 |
| Osmolarity | 277 mOsmol | 270 mOsmol |
| Phospholipid proportions (stroma) | not detectable lower limit of detection: 1 μg/ml | not detectable lower limit of detection: 1 μg/ml |
| K.O.D. | 4.51 kPa (33.9 mm Hg) | 3.95 kPa (29.7 mm Hg) |
| Viscosity (capillary viscosimeter according to Ubbelohde) | 1.45 cSt | 0.96 cSt |

Example 2

Preparation of a heparin fragment from mucosa-heparin by $NaIO_4$ treatment

Two grams of commercially available sodium heparin (mucosa) having a molecular weight of 13,500 are dissolved in 40 ml of a 50 mM sodium acetate buffer (pH 4.0; adjusted with acetic acid). Then 140 mg of $NaIO_4$ incubation are added, followed by an incubation in the absence of light at from 2 to 4° C. for 6 hours. The molar ratio of heparin/$NaIO_4$ is 1/4.2.

Then the pH value is adjusted to 12.0 with 3N NaOH and re-adjusted to 7.0 after 30 minutes (4N HCl). This is followed by a dialysis in Cuprophan dialysis tubes (cut-off=1,000 D) until chloride ions are not any more detectable in the dialyzate (titration with 0.1N $AgNO_3$). Finally the material is lyophilized or spray-dried.

The following analytical data were found for the heparin fragment prepared according to this variant:

Molecular weight: 2,400 D; aldehyde content: 0.45 μmol/mg.

One thousand milliliters of a hemoglobin solution (64 mg/ml of Hb A) are first deoxygenated under nitrogen—as in Example 1—and incubated with 10 g of the heparin fragment reacted with periodate at room temperature for 3 hours. The molar ratio of hemoglobin to heparin fragment is 1:5.

A sample (0.5 ml) of the reaction mixture is de-salted on a column equilibrated with BISTRIS buffer (Sephadex G 75, Pharmacia Fine Chemicals, Uppsala; 1 cm×18 cm; flow rate: 1 ml/30 min). Control tests showed that under these conditions hemoglobin is separated from heparin fragment that has not been reacted with Hb under the employed conditions and remained in the reaction mixture. The de-salted hemoglobin solution is re-concentrated to a hemoglobin content of 7.3% by ultrafiltration, and the oxygen binding curve was measured. A P 50 value of 7.33 kPa (55 mmHg) was determined.

Chromatography on Mono S ion exchanger showed a peak group ratio of 65.4/34.6 (cf. FIG. 5) and, thus, a conversion rate of 60.68% (native Hb lysate shows a peak group ratio of 12/88 in the chromatogram of Mono S-FPLC).

Example 3

Preparation of a heparin fragment from mucosa-heparin by a method of combined degradation using $NaNO_2/NaIO_4$ 3.1

Ten grams of sodium heparin (mucosa) were dissolved in 200 ml of a 50 mM sodium acetate solution (pH 4.0; to be adjusted with acetic acid) and admixed with 80 ml of a 4% $NaNO_2$ solution.

The mixture is stirred at room temperature for 3.5 h; then 5 g (=25 mmol) of $NaIO_4$ are added, followed by incubation at 2 to 4° C. for 48 hours. Thereafter the mixture is dialyzed or diafiltrated until $IO_4^-$ and $NO_2^-$ ions are no longer detectable in the dialyzate or diafiltrate [detection of the $NO_2^-$ ions with "Aquaquant" (Merck AG)]. The solid reaction product is recovered by lyophilization.

The following analytical data were measured for the heparin fragment:

Molecular weight: 2,100 D

Aldehyde content: 0.55 μmol/mg.

3.2

After incubation of a hemoglobin solution with the heparin fragment 3.1 (molar ratio Hb/heparin=1/5) under the conditions described in Example 2 the heparin fragment-hemoglobin adduct was isolated. A P 50 value of 8.14 kPa (61.1 mm Hg) was measured.

Mono S: Peak group ratio (cf FIG. 5) 68.2/31.8 (Conversion rate: 63.8%).

Example 4

Preparation of a heparin fragment from "high affinity" heparin 4.1

Commercially available heparin can be separated by affinity chromatography on anti-thrombin III (AT III), a glycoprotein occurring in human plasma, which has been coupled to sepharose, into three different fractions which are distinguished from each other by the strengths of their bonds to AT III (no affinity, low affinity und high affinity heparin) [J. Hopwood, M. Höök, A. Linker, U. Lindahl, FEBS-Letters 69, 51–54 (1976)].

The analytical or preparative separation of heparin into said fractions is familiar to the artisan.

It has been shown that particularly the fraction being bound to AT III with high affinity (high affinity heparin) or the degradation products thereof (method according to Example 1) react with hemoglobin in same manner as observed with commercially available heparin.

For said heparin fragment the following data were measured:
Molecular weight: 7,000 D
Aldehyde content: 0.45 μmol/mg.

4.2

After incubation of a hemoglobin solution with the heparin fragment 4.1 (molar ratio Hb/heparin=1/5) under the conditions described in Example 2 the hemoglobin-heparin fragment adduct was isolated. A P 50 value of 5.98 kPa (44.9 mm Hg) was measured.

Chromatography on Mono S: Peak group ratio (cf. FIG. 5) 68.2/31.8 (Conversion rate: 57.7%).

Example 5

Preparation of a heparin fragment from bovine lung heparin ("type B" heparin)

5.1

Bovine lung heparin (Hepar Industries, Inc., Ohio, U.S.A.) was subjected to a degradation with $HNO_2$ according to Example 1. The following analytical data were measured with the obtained product:
Molecular weight: 2,600 D
Aldehyde content: 0.44 μmol/mg.

5.2

After incubation of a hemoglobin solution with the heparin fragment 5.1 (molar ratio Hb/heparin=1/1) under the conditions described in Example 2 the heparin fragment-hemoglobin adduct was isolated. A P 50 value of 3.26 kPa (24.45 mm Hg) was measured.

Chromatography on Mono S: Peak group ratio 62/38 (Conversion rate: 56.8%).

Example 6

Preparation of a heparin fragment from heparin of ointment quality 6.1

Ointment grade heparin was degraded according to Example 1. The following product data were obtained:
Molecular weight: 2,600 D
Aldehyde content: 0.44 μmol/mg.

6.2

After incubation of a hemoglobin solution with the heparin fragment 6.1 (molar ratio Hb/heparin=1/5) under the conditions described in Example 2 the heparin fragment-hemoglobin adduct was isolated. A P 50 value of 5.32 kPa (40 mm Hg) was measured.

Chromatography on Mono S: Peak group ratio 60/40 (Conversion rate: 54.5%).

Example 7

Preparation of monosaccharide fragments from heparan sulfate or dermatan sulfate 7.1

Other sulfated glycosaminoglykans are also degradable by using the methods described in the Examples 1 to 3, and the degradation products are usable as effectors for the reaction with hemoglobin.

According to Example 1 there were fragmented (a) heparan sulfate and (b) dermatan sulfate (Sigma Chemie GmbH., St. Louis, U.S.A./Calbiochem).

The following product data were obtained:
Molecular weight: (a) 400 to 650 D; (b) 500 to 700 D
Aldehyde content: (a) 2.2 μmol/mg; (b) 1.8 μmol/mg.

7.2

After incubation of a hemoglobin solution with the fragments of 7.1 under the conditions described in Example 2 the hemoglobin-fragment adducts were isolated. The measured P 50 values were (a) 5.58 kPa (41.9 mmHg) and (b) 5.25 kPa (33.4 mm Hg), respectively.

Chromatography on Mono S: Peak group ratio 65/35 (Conversion rate: 60.22%).

Example 8

8.1 Sulfation of heparin

Into commercially available heparin sodium having 162 I.U./mg (according to U.S.P. XX) sulfate groups are introduced for increasing the sulfate content thereof in accordance with the procedure described by C. R. Ricketts, Biochem. J. 51, 129–133 (1952), "Dextrane sulphate—a synthetic analogue of heparin"; the obtained "supersulfated" heparin was isolated and reacted in a consecutive step with $HNO_2$ according to Example 1.

Forty-four millilters of chlorosulfonic acid are dropwise added to 200 ml of vigorously stirred pyridine dried over molecular sieve. During this procedure the mixture must be cooled with dry ice/ethanol because of the strong heat evolution. Then the temperature is increased to 65° C., and 30 g of finely powdered heparin dried in vacuo at 50° C. are added portionwise. The mixture is maintained at 65° C. to 70° C. for 4 hours, allowed to cool to room temperature and then poured onto 800 ml of ice, when a 40% (w/v) sodium hydroxide solution is added, until the color of the mixture turns to dark red. Two phases are formed. The upper phase (pyridine) is removed in a separating funnel. The lower phase is admixed at 4° C. with 2 liters of cooled ethanol. Thereby the sulfated heparin is precipitated. The mixture is allowed to sit for 12 hours at 4° C. and then decanted. The residue is taken up in 200 ml of water and in a Cuprophan tube dialyzed against water at 4° C. for 48 hours. The dialyzed solution is lyophilized to recover the heparin derivative.
Yield: 22 g (73%, based on heparin)
Analysis: free sulfate not detectable
Anticoagulative activity: 195 U/mg according to U.S.P. XX.
Sulfur content: 13.1%

The sulfur content of the heparin employed in the sulfation is 10.2%.

8.2 Degradation of the heparin sulfated according to 8.1.

Ten grams of the heparin derivative prepared according to 8.1 were reacted with $HNO_2$ at pH 4.0 in accordance with the procedure according to Example 1. dialyzed in a Cuprophan dialysis tube until nitrite-free and lyophilized to recover the solid substance. 6.6 g of the HNO$_2$ degradation product were isolated.

The anticoagulative activity according to U.S.P. XX is 1.3 I.U./mg.

Aldehyde content: 0.57 μmol/mg
Molecular mass distribution: 1,500 to 2,500 D
Average molecular weight: 1,700 D.
8.3

The heparin degradation product obtained according to 8.2 is reacted with hemoglobin solution according to the prescription given in Example 1.3.

250 ml of deoxygenated hemoglobin lysate having a hemoglobin content of 5.3% are reacted with 0.88 g of heparin fragment of 8.2 under the conditions described in Example 1 at room temperature for 5 hours. The reaction mixture is diafiltrated with 2 liters of N$_2$-purged 225 mM BISTRIS buffer, pH 7.4 (37° C.) in an Amicon stirrer-equipped cell. Evaluation of the oxygen binding curve resulted in a P 50 value 8.91 kPa (66.8 mm Hg).

We claim:

1. A stroma-free blood substitute consisting essentially of an aqueous medium containing the covalently linked adducts of sulfated glycosaminoglycan fragments having molecular weights from 1000 to 10,000 daltons with hemoglobin, the proportion of said fragments and of said hemoglobin being such that the oxygen binding property of said adducts is from 4.79 kPa to 9.33 kPa partial pressure of oxygen.

2. A stroma-free blood substitute as claimed in claim 1 in which said oxygen binding property is from 5.32 kPa to 7.98 kPa partial pressure of oxygen.

3. A stroma-free blood substitute as claimed in claim 1 or 2 in which said fragments are selected from the group consisting of fragments of heparin, heparinoid, dermatan sulfate, heparin sulfate, sulfated chitin or sulfated chitosan.

4. A stroma-free blood substitute as claimed in claim 1 or 2 in which said fragments are fragments of heparin.

5. A stroma-free blood substitute as claimed in claim 4 in which said fragments are made by degrading heparin with nitrate.

6. A stroma-free blood substitute as claimed in claim 4 in which the molar ratio of hemoglobin to fragments of heparin is from 1:0.4 to 1:5 based of an assumed molecular weight of hemoglobin of 64,500 daltons and an assumed molecular weight of heparin fragments of 2000 daltons.

7. A stroma-free blood substitute as claimed in claim 4 in which the mass ratio of heparin fragments to hemoglobin is from 1:7 to 1:84.

8. A stroma-free blood substitute as claimed in claim 5 in which said heparin fragments are obtained by degradation of heparin and contain an aldehyde group, and the molar ratio of hemoglobin to aldehyde content of said fragments is from 1:0.4 to 1:5 based on an assumed molecular weight of hemoglobin of 64,500 daltons and an assumed aldehyde content of 0.5 mmol/mg of heparin fragments.

9. Process for preparing a blood substitute as claimed in claim 1 comprising mixing said glycosaminoglycan fragments in an aqueous medium at pH 5.5 to 8.5 containing 0.5 to 40% by weight of oxygenated or deoxygenated hemoglobin at a temperature from 2° to 60° C. to cause a reaction between said fragments and said hemoglobin, and diafiltering said mixture against a buffer at pH 7.1 to 7.8.

10. Process as claimed in claim 9 in which said hemoglobin is deoxygenated hemoglobin, said aqueous medium is at pH 7.1 to 7.8, the concentration of said hemoglobin is from 5 to 9% by weight, and said temperature is from 10° to 30° C.

11. Process as claimed in claim 10 in which said reaction is carried out in the absence of oxygen.

12. Process as claimed in claim 9, 10 or 11 in which said aqueous solution contains a buffer and the concentration of buffering ions is from 0.05 to 1 molar.

13. Process as claimed in claim 9, 10 or 11 in which said fragments are fragments of heparin and are incubated in a buffered aqueous medium isotonic to erythrocytes and containing intact erythrocytes, the molar ratio of hemoglobin in said erythrocytes to said fragments of heparin being from 1:0.4 to 1:20 based on an assumed molecular weight of hemoglobin of 64,500 daltons and an assumed molecular weight of heparin fragment of 2000 daltons.

14. Process as claimed in claim 9, 10 or 11 including the additional step of reducing the reaction products of said fragments and said hemoglobin by the addition of sodium borohydride.

15. Process as claimed in claim 9, 10 or 11 including the additional step of cross-linking the reaction products of said fragments and said hemoglobin by the addition of a polyfunctional cross-linking agent 16. Process as claimed in claim 15 in which said cross-linking agent is glutardialdehyde.

17. A stroma-free blood substitute as claimed in claim 5 in which the molar ratio of hemoglobin to fragments of heparin is from 1:0.4 to 1:5 based on an assumed molecular weight of hemoglobin of 64,500 daltons and an assumed molecular weight of heparin fragments of 2000 daltons.

18. A stroma-free blood substitute as claimed in claim 5 in which the mass ratio of heparin fragments to hemoglobin is from 1:7 to 1:84.

* * * * *

UNITED STATES PATENT AND TRADEMARK OFFICE
CERTIFICATE OF CORRECTION

PATENT NO. : 4,920,194

DATED : April 24, 1990

INVENTOR(S) : Wolfgang Feller et al.

It is certified that error appears in the above-identified patent and that said Letters Patent is hereby corrected as shown below:

Col. 16, line 20, "(7B)" should be --(7A)--

Col. 20, line 18, "HASHED" should be --$HBA_{1c}$--

Col. 21, line 58, delete "incubation" before "are added,"

Col. 25, line 44, "nitrate" should be --nitrite--

Signed and Sealed this

First Day of October, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,920,194

DATED : April 24, 1990

INVENTOR(S) : Feller, et al

It is certified that error appears in the above-identified patent and that said Letters Patent is hereby corrected as shown below:

On the title page:

Add the following cited references to the list of OTHER PUBLICATIONS:

P. Labrude et al., Hemoglobin Solutions as Oxygen Carriers: Ligands and other Molecules Interations with Hemoglobin in: ADV. BIOSC. 1986, 54 (Oxygen Transp. Red Blood Cells), Page 16 ET SEQ.

Amiconi, G. et al., Eur. J. Biochem., Vol. 76, PP. 339-343 (1977).

Interaction between Human Hemoglobin and Sulfated Polysaccharides: Identification of the Binding Site and Specificity in: Affinity Chromatography and Biological Recognition, ED. 1.M. Chaiken, M. Wilchek, I. Parikh, Academic Press, 1983.

Signed and Sealed this

Fifth Day of November, 1991

*Attest:*

HARRY F. MANBECK, JR.

*Attesting Officer*   *Commissioner of Patents and Trademarks*